(12) United States Patent
Cox et al.

(10) Patent No.: US 8,211,005 B2
(45) Date of Patent: *Jul. 3, 2012

(54) METHOD AND APPARATUS FOR TREATING PELVIC ORGAN PROLAPSE

(75) Inventors: James E. Cox, Corcoran, MN (US); Kimberly A. Anderson, Eagan, MN (US); Robert E. Lund, St. Michael, MN (US); Brian P. Watschke, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 650 days.

This patent is subject to a terminal disclaimer.

(21) Appl. No.: 12/321,546

(22) Filed: Jan. 22, 2009

(65) Prior Publication Data
US 2009/0137864 A1 May 28, 2009

Related U.S. Application Data

(63) Continuation of application No. 10/834,943, filed on Apr. 30, 2004, now Pat. No. 7,500,945.

(51) Int. Cl.
*A61F 2/00* (2006.01)
(52) U.S. Cl. ........................................ 600/37
(58) Field of Classification Search .................. 600/29, 600/30, 37; 128/885; 606/151
See application file for complete search history.

(56) References Cited

U.S. PATENT DOCUMENTS

| | | |
|---|---|---|
| 2,738,790 A | 3/1956 | Todt et al. |
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |

(Continued)

FOREIGN PATENT DOCUMENTS

DE   23 05 815 A1   8/1974

(Continued)

OTHER PUBLICATIONS

"Urinary Incontinence: Easier Operation" Article from La Libre Belgique, Wednesday, Oct. 15, 2003 (English translation provided).

(Continued)

*Primary Examiner* — Charles A Marmor, II
*Assistant Examiner* — Christine Hopkins
(74) *Attorney, Agent, or Firm* — Kimberly K. Baxter; Gregory L. Koeller

(57) ABSTRACT

A method of treating pelvic organ prolapse is provided. The method generally includes the steps of establishing a first pathway between the external perirectal region of the patient to the region of the ischial spine in tissue on one side of the prolapsed organ, followed by establishing a second pathway in tissue on the contralateral side of the prolapsed organ. A support member, which includes a central support portion and two end portions, is positioned in a position to reposition said prolapsed organ in said organ's anatomically correct location. The end portions of the support member are introduced through the respective tissue pathways, followed by adjustment of the end portions so that the support member is located in a therapeutic relationship to the prolapsed organ that is to be supported. An apparatus and kit for said treatment is further provided.

22 Claims, 9 Drawing Sheets

U.S. PATENT DOCUMENTS

| | | | |
|---|---|---|---|
| 3,763,860 A | 10/1973 | Clarke |
| 3,789,828 A | 2/1974 | Schulte |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,204,541 A | 5/1980 | Kapitanov |
| 4,235,238 A | 11/1980 | Ogiu et al. |
| 4,246,660 A | 1/1981 | Wevers |
| 4,265,231 A | 5/1981 | Scheller, Jr. et al. |
| 4,441,497 A | 4/1984 | Paudler |
| 4,509,516 A | 4/1985 | Richmond |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,920,986 A | 5/1990 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,188,636 A | 2/1993 | Fedotov |
| 5,207,694 A | 5/1993 | Broome |
| 5,209,756 A | 5/1993 | Seedhom et al. |
| 5,250,033 A | 10/1993 | Evans et al. |
| 5,256,133 A | 10/1993 | Spitz |
| 5,281,237 A | 1/1994 | Gimpelson |
| 5,328,077 A | 7/1994 | Lou |
| 5,336,239 A | 8/1994 | Gimpelson |
| 5,337,736 A | 8/1994 | Reddy |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,520,700 A | 5/1996 | Beyar et al. |
| 5,520,703 A | 5/1996 | Essig et al. |
| 5,544,664 A | 8/1996 | Benderev et al. |
| 5,562,685 A | 10/1996 | Mollenauer et al. |
| 5,562,689 A | 10/1996 | Green et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,662,683 A | 9/1997 | Kay |
| 5,669,935 A | 9/1997 | Rosenman et al. |
| 5,683,349 A | 11/1997 | Makower et al. |
| 5,807,403 A | 9/1998 | Beyar et al. |
| 5,810,882 A | 9/1998 | Bolduc et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,904,696 A | 5/1999 | Rosenman |
| 5,919,232 A | 7/1999 | Chaffringeon et al. |
| 5,934,283 A | 8/1999 | Willem et al. |
| 5,935,122 A | 8/1999 | Fourkas et al. |
| 5,935,138 A | 8/1999 | McJames, II et al. |
| 5,944,732 A | 8/1999 | Raulerson et al. |
| 5,972,000 A | 10/1999 | Beyar et al. |
| 5,988,171 A | 11/1999 | Sohn et al. |
| 5,992,269 A | 11/1999 | Puig et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,042,534 A | 3/2000 | Gellman et al. |
| 6,042,536 A | 3/2000 | Tihon et al. |
| 6,048,351 A | 4/2000 | Gordon et al. |
| 6,050,937 A | 4/2000 | Benderev |
| 6,053,935 A | 4/2000 | Brenneman et al. |
| 6,068,591 A | 5/2000 | Bruckner et al. |
| 6,071,290 A | 6/2000 | Compton |
| 6,099,538 A | 8/2000 | Moses et al. |
| 6,106,545 A | 8/2000 | Egan |
| 6,110,101 A | 8/2000 | Tihon et al. |
| 6,117,067 A | 9/2000 | Gil-Vernet |
| 6,168,611 B1 | 1/2001 | Risvi |
| 6,221,005 B1 | 4/2001 | Bruckner et al. |
| 6,273,852 B1 | 8/2001 | Lehe et al. |
| 6,302,840 B1 | 10/2001 | Benderev |
| 6,306,079 B1 | 10/2001 | Trabucco |
| 6,328,744 B1 | 12/2001 | Harari et al. |
| 6,334,446 B1 | 1/2002 | Beyar |
| 6,352,553 B1 | 3/2002 | van der Burg et al. |
| 6,367,353 B2 | 4/2002 | Puig et al. |
| 6,382,214 B1 | 5/2002 | Raz et al. |
| 6,406,423 B1 | 6/2002 | Scetbon |
| 6,406,480 B1 | 6/2002 | Beyar et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,494,906 B1 | 12/2002 | Owens |
| 6,502,578 B2 | 1/2003 | Raz et al. |
| 6,530,943 B1 | 3/2003 | Hoepffner et al. |
| 6,582,443 B2 | 6/2003 | Cabak et al. |
| 6,626,917 B1 | 9/2003 | Craig |
| 6,663,633 B1 | 12/2003 | Pierson, II |
| 7,500,945 B2 * | 3/2009 | Cox et al. ........................ 600/37 |
| 7,766,926 B2 * | 8/2010 | Bosley et al. .................. 606/151 |
| 2001/0000533 A1 | 4/2001 | Kovac |
| 2001/0049467 A1 | 12/2001 | Lehe et al. |
| 2002/0022841 A1 | 2/2002 | Kovac |
| 2002/0028980 A1 | 3/2002 | Thierfelder et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslaine et al. |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0165566 A1 | 11/2002 | Ulmsten |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023137 A1 | 1/2003 | Gellman |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0045892 A1 | 3/2003 | Kaladelfos |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0100954 A1 | 5/2003 | Schuldt-Hempe et al. |
| 2003/0114866 A1 | 6/2003 | Ulmsten et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176762 A1 | 9/2003 | Kammerer |
| 2003/0191480 A1 | 10/2003 | Ulmsten et al. |
| 2003/0199732 A1 | 10/2003 | Suslian et al. |
| 2003/0220538 A1 | 11/2003 | Jacquetin |
| 2004/0039453 A1 | 2/2004 | Anderson et al. |
| 2004/0116774 A1 | 6/2004 | Migliari |

| | | | |
|---|---|---|---|
| 2004/0144395 | A1 | 7/2004 | Evans et al. |
| 2004/0249473 | A1 | 12/2004 | Delorme et al. |
| 2005/0004426 | A1 | 1/2005 | Raz et al. |
| 2005/0065395 | A1 | 3/2005 | Mellier |

FOREIGN PATENT DOCUMENTS

| | | |
|---|---|---|
| DE | 42 20 283 C2 | 12/1993 |
| DE | 43 04 353 A1 | 4/1994 |
| DE | 101 38 950 A1 | 2/2003 |
| DE | 102 11 360 A1 | 10/2003 |
| EP | 0 470 308 A1 | 2/1992 |
| EP | 0 643 945 A2 | 3/1995 |
| EP | 0 650 703 A1 | 5/1995 |
| EP | 1 093 758 A1 | 4/2001 |
| SU | 1225547 A | 4/1986 |
| SU | 1342486 A1 | 10/1987 |
| WO | WO 93/17635 A1 | 9/1993 |
| WO | WO 93/19678 A2 | 10/1993 |
| WO | WO 97/16121 A1 | 5/1997 |
| WO | WO 98/19606 A1 | 5/1998 |
| WO | WO 98/35606 A2 | 8/1998 |
| WO | WO 98/35616 A1 | 8/1998 |
| WO | WO 98/35632 A1 | 8/1998 |
| WO | WO 99/52450 A1 | 10/1999 |
| WO | WO 00/13601 A1 | 3/2000 |
| WO | WO 00/18319 A1 | 4/2000 |
| WO | WO 00/57812 A1 | 10/2000 |
| WO | WO 00/64370 A1 | 11/2000 |
| WO | WO 00/74594 A1 | 12/2000 |
| WO | WO 00/74613 A1 | 12/2000 |
| WO | WO 00/74633 A2 | 12/2000 |
| WO | WO 01/26581 A1 | 4/2001 |
| WO | WO 01/39670 A1 | 6/2001 |
| WO | WO 01/45589 A1 | 6/2001 |
| WO | WO 01/56499 A1 | 8/2001 |
| WO | WO 01/78609 A2 | 10/2001 |
| WO | WO 02/02031 A1 | 1/2002 |
| WO | WO 02/19944 A2 | 3/2002 |
| WO | WO 02/26108 A2 | 4/2002 |
| WO | WO 02/28312 | 4/2002 |
| WO | WO 02/32284 A2 | 4/2002 |
| WO | WO 02/34124 A2 | 5/2002 |
| WO | WO 02/38079 A2 | 5/2002 |
| WO | WO 02/39890 A2 | 5/2002 |
| WO | WO 02/069781 A2 | 9/2002 |
| WO | WO 02/071953 A2 | 9/2002 |
| WO | WO 02/078552 A1 | 10/2002 |
| WO | WO 2004/016196 A2 | 2/2004 |
| WO | WO 2004/019786 A1 | 3/2004 |

OTHER PUBLICATIONS

Aldridge, Albert H., B.S., M.D., F.A.C.S., "Transplantation of Fascia for Relief of Urinary Stress Incontinence" Am. J. of Obstet. and Gynec., vol. 44, pp. 398-411 (1948).
Araki, Tohru, et al, "The Loop-Loosening Procedure for Urination Difficulties After Stamey Suspension of the Vesical Neck" The Journal of Urology, vol. 144, pp. 319-323, (Aug. 1990) American Urological Association, Inc.
Asmussen, M., et al "Simultaneous Urethro-Cystometry With a New Technique" Scand J Urol Nephro) 10, pp. 7 11 (1976).
Beck, Peter R. et al., "Treatment of Urinary Stress Incontinence With Anterior Colporrhaphy" Obstetrics and Gynecology, vol. 59 (No. 3), pp. 269-274 (Mar. 1982).
Benderev, Theodore V., M.D., "Anchor Fixation and Other Modifications of Endoscopic Bladder Neck Suspension" Urology, vol. 40, No. 5, pp. 409-418 (Nov. 1992).
Benderev, Theodore V., MD, "A Modified Percutaneous Outpatient Bladder Neck Suspension System" Journal of Urology, vol. 152, pp. 2316-2320 (Dec. 1994).
Bergman, Arieh, M.D. et al., "Three surgical procedures for genuine stress incontinence: Five-year follow-up of a prospective randomized study" Am. J. Obstet Gynecol, vol. 173 No. 1, pp. 66-71 (Jul. 1995).
Blaivas, Jerry G., "Commentary: Pubovaginal Sling Procedure" Surgery for Female Urinary Incontinence, pp. 93-101 (1990).
Blaivas, Jerry G., et al., "Pubovaginal Fascial Sling for the Treatment of Complicated Stress Urinary Incontinence" The Journal of Urology, vol. 145, pp. 1214-1218 (Jun. 1991) American Urological Association, Inc.
Blaivas, Jerry G., M.D., et al., "Type III Stress Urinary Incontinence: Importance of Proper Diagnosis and Treatment" Gynecology and Obstetrics Surgical Forum , 35, pp. 473-475 (1984).
Bryans, Fred E., M.D., F.R.C.S.(C.), "Marlex gauze hammock sling operation with Cooper's ligament attachment in the management of recurrent urinary stress incontinence" Am. J. Obstet. Gynecol., vol. 133, No. 3, pp. 292-294 (Feb. 1, 1979).
Burch, John C., M.D., "Urethrovaginal fixation to Cooper's ligament for correction of stress incontinence, cystocele, and prolapse" Am. J. Obstet. & Gynecol., vol. 81 No. 2, pp. 281-290 (Feb. 1961).
Choe, Jong M., et al., "Gore-Tex Patch Sling: 7 Years Later" Urology, 54 (4) pp. 641-646 (1999) Elsevier Science Inc.
Chu, C.C., and Welch, L., "Characterization of Morphologic and Mechanical Properties of Surgical Mesh Fabrics" Journal of Biomedical Materials Research, vol. 19, pp. 903-916 (1985) ©1985 John Wiley & Sons, Inc.
Dargent, D., et al. Pose d'un ruban sous uretral oblique par voie obturatrice dans le traitement de l'incontinence urinaire feminine, Gynecol Obstet Fertil 2002; 30: pp. 576-582 (2002) (English translation provided).
Das, Sakti at al., "Laparoscopic Colpo-Suspension" The Journal of Urology, vol. 154, pp. 1119-1121 (Sep. 1995).
de Leval, Jean "Novel Surgical Technique for the Treatment of Female Stress Urinary Incontinence: Transobturator Vaginal Tape Inside-Out" European Urology 44 pp. 724-730 (2003).
Decter, Ross M., "Use of the Fascial Sling for Neurogenic Incontinence: Lessons Learned" The Journal of Urology, vol. 150, pp. 683-686, (Aug. 1993) American Urological Association, Inc.
DeLancey, John 0. L., M.D., "Structural support of the urethra as it relates to stress urinary incontinence: The hammock hypothesis" Am. J Obstet Gynecol, pp. 1713-1723 (Jun. 1994).
Delorme, "La bandelette trans-obturatrice: on procede mini-invasif pour traiter l'incontinence urinaire d'effort de la femme", Urologie de la Femme, Progres en Urologie (2001), 11, 1306-1313 (Sep. 2001) (English translation provided).
Delorme, Emmanuel et al., "Transobturator Tape (Uratape®): A New Minimally-Invasive Procedure to Treat Female Urinary Incontinence" European Urology 45 (2004) 203-207 (Dec. 2003).
Dietz, H.P., et al., "Mechanical Properties of urogynecologic Implant Materials" International Urogynecology Journal (2003) 14:239-243 (Aug. 5, 2003).
Enzelsberger, H., et al., "Urodynamic and Radiologic Parameters Before and After Loop Surgery for Recurrent Urinary Stress Incontinence" Acta Obstet Gynecol Scand 1990; 69 pp. 51-54 (1990).
Eriksen, Bjarne C., et al., "Long-Term Effectiveness of the Burch Colposuspension in Female Urinary Stress Incontinence" Acta Obstet Gynecol Scand 1990; 69 pp. 45-50 (1990).
Falconer, C. et al., "Clinical Outcome and Changes in Connective Tissue Metabolism After Intravaginal Slingplasty in Stress Incontinent Women" International Urogynecol J, vol. 7, pp. 133-137, (1996).
Falconer, C., et al., "Influence of Different Sling Materials on Connective Tissue Metabolism in Stress Urinary Incontinent Women" International Urogynecology Journal, (2001) (Supp. 2) pp. S19-S23 (2001).
Gilja, Ivan et all, "A Modified Raz Bladder Neck Suspension Operation (Transvaginal Burch)" The Journal of Urology, vol. 153, pp. 1455-1457 (May 1995).
Gittes, Ruben F., et al, "No-Incision Pubovaginal Suspension for Stress Incontinence" The Journal of Urology, vol. 138, pp. 568-570 (Sep. 1987).
Handa, Victoria L., M.D. et al., "Banked Human Fascia Lata for the Suburethral Sling Procedure: A Preliminary Report" Obstetrics and Gynecology, vol. 88, No. 6, pp. 1045-1049 (Dec. 1996).
Henriksson, L., M.D. et al., "A urodynamic evaluation of the effects of abdominal urethrocystopexy and vaginal sling urethroplasty in women with stress incontinence" Am. J. Obstet. Gynecol, pp. 77-82 (May 1, 1978).
Hershorn, Sender, M.D. et al., "Gynecare TVT With Abdominal Guides Early Clinical Experience" Gynecare TVT, Marketing Material, Gynecare Worldwide (May 2002), 12 pages.

Hodgkinson, C. Paul, M.D., et al., "Urinary Stress Incontinence in the Female—III. Round-ligament technic for retropubic suspension of the urethra" Obstetrics and Gynecology, vol. 10, No. 5, pp. 493-499 (Nov. 1957).

Hohenfellner, Rudolf, et al., "Sling Procedures" Surgery of Female Incontinence—Second Edition, Chapter 7, pp. 105-113, Springer-Verlag (May 1, 1986).

Holschneider, C.H., et al., "The Modified Pereyra Procedure in Recurrent Stress Urinary Incontinence: A 15-year Review" Obstetrics & Gynecology, vol. 83, No. 4, pp. 573-578 (Apr. 1994).

Horbach, Nicollette S., "Suburethral Sling Procedures" Urolgynecology and Urodynamics Theory and Practice, Fourth Edition, Chapter 42, pp. 569-579, Williams & Wilkins (1996).

Horbach, Nicollette S., et al., "A Suburethral Sling Procedure with Polytetrafluoroethylene for the Treatment of Genuine Stress Incontinence in Patients with Low Urethral Closure Pressure" Obstetrics & Gynecology, vol. 71, No. 4, pp. 648-652 (Apr. 1988).

Iglesia, C.B., et al., "The Use of Mesh in Gynecologic Surgery" International Urogynecology Journal (1997) 8:105-115, Springer-Verlag London Ltd. (1997).

Ingelman-Sundberg, A., et al., "Surgical Treatment of Female Urinary Stress Incontinence" Contr. Gynec. Obstet. vol. 10, pp. 51-69 (Karger. Basel 1983).

Jeffcoate, T. N. A., M.D., F.R.C.S.E., F.R.C.O.G., "The Results of the Aldridge Sling Operation for Stress Incontinence" J Obstet Gynaecol Br Emp., 63(1) pp. 36-39 (Feb. 1956).

Karram, Mickey M., M.D. et al., "Patch Procedure: Modified Transvaginal Fascia Lata Sling for Recurrent or Severe Stress Urinary Incontinence" Obstetrics & Gynecology, vol. 75, No. 3, Part 1, pp. 461-463 (Mar. 1990).

Kersey, J., "The gauze hammock sling operation in the treatment of stress incontinence" British Journal of Obstetrics and Gynaecology, vol. 90 pp. 945-949, (Oct. 1983).

Klutke, Carl et al., "The Anatomy of Stress Incontinence: Magentic Resonance Imaging of the Female Bladder Neck and Urethra" The Journal Urology, vol. 143, pp. 563-566 (Mar. 1990).

Klutke, John James et al., "Transvaginal Bladder Neck Suspension to Cooper's Ligament: A Modified Pereyra Procedure" Obstetrics & Gynecology, vol. 88, No. 2, pp. 294-96 (Aug. 1996).

Klutke, John, M.D. et al., "The promise of tension-free vaginal tape for female SUI" Contemporary Urology, pp. 59-60, 65-66, 69-70, 73 (Oct. 2000).

Korda, Andrew, et al., "Expe ience with Silastic Slings for Female Urinary Incontinence" Aust NZ J Obstet Gynaecol, vol. 29, pp. 150-154 (1989).

Kovac, S. Robert, et al, "Pubic Bone Suburethral Stabilization Sling for Recurrent Urinary Incontinence" Obstetrics & Gynecology, vol. 89, No. 4, pp. 624-627 (Apr. 1997).

Kovac, S. Robert, et al, "Pubic Bone Suburethral Stabilization Sling: A Long Term Cure for SUI?" Contemporary OB/GYN, 8 pages (Feb. 1998).

Kovac, S. Robert, "Follow-up of the Pubic Bone Suburethral Stabilization Sling Operation for Recurrent Urinary Incontinence (Kovac Procedure)" Journal of Pelvic Surgery, pp. 156-160 (May 1999).

Leach, Gary E., et al, "Female Stress Urinary Incontinence Clinical Guidelines Panel Report on Surgical Management of Female Stress Urinary Incontinence" American Urological Association, vol. 158, pp. 875-880 (Sep. 1997).

Leach, Gary E., Md, "Bone Fixation Technique for Transvaginal Needle Suspension" Urology vol. XXXI, No. 5, pp, 388-390 (May 1988).

Letters to the Editor, R. Villet's response to the article by D. Dargent et al., "Placement of an oblique transobturator suburethral tape in the treatment of female urinary incontinence", Gynecology Obstetrics & Fertility 31, pp. 96-101 (2003) (English translation provided).

Lichtenstein, Irving L., M.D., et al., "The Tension-Free Hernioplasty" The American Journal of Surgery, vol. 157, pp. 188-193 (Feb. 1989).

Loughlin, Kevin R., et al., "Review of an 8-Year Experience With Modifications of Endoscopic Suspension of the Bladder Neck for Female Stress Urinary Incontinence" The Journal of Urology, vol. 143, pp. 44-45 (Jan. 1990).

Marshall, Victor Fray, M.D., F.A.C.S. et al., "The Correction of Stress Incontinence by Simple Vesicourethral Suspension" Surgery, Gynecology and Obstetrics, vol. 88, pp. 509-518 (1949).

Mascio, Valenzio C., M.D., "Therapy of Urinary Stress Incontinence in Women Using Mitek GII Anchors" Mitek Surgical Products, Inc., 5 pages (1993).

McGuire, Edward J. et al., "Abdominal Fascial Slings" Female Urology 2nd ed. (Raz. S. ed.). W.B. Saunders Company, Chapter 31, pp. 369-375 (1996).

McGuire, Edward J. et al., "Experience With Pubovaginal Slings for Urinary Incontinence at the University of Michigan" The Journal of Urology, vol. 138, pp. 525-526 (Sep. 1987).

McGuire, Edward J., et al., "Pubovaginal Sling Procedure for Stress Incontinence" The Journal of Urology, vol. 119, pp. 82-84 (Jan. 1978) The Williams & Wilkins Co.

McGuire, Edward J., M.D., "Abdominal Procedures for Stress Incontinence" Symposium on Female Urology, Urologic Clinics of North America—vol. 12, No. 2, pp. 285-290 (May 1985).

McIndoe, G. A. J., et al., "The Aldridge Sling Procedure in the Treatment of Urinary Stress Incontinence" Aust NZ J Obstet Gynaecol, vol. 27, pp. 238-239 (1987).

McKiel, Charles F., Jr. et al., "Marshall-Marchetti Procedure: Modification" 1st Journal in Urology, vol. 96, pp. 737-739 (Nov. 1966) The Williams & Wilkins Co.

Moir, J. Chassar, "The Gauze-Hammock Operation (A Modified Aldridge Sling Prcedure)" The Journal of Obstetrics and Gynaecology of the British Commonwealth, vol. 75 No. 1, pp. 1-9 (Jan. 1968).

Morgan, J.E., M.D. et al., "The Marlex Sling Operation for the Treatment of Recurrent Stress Urinary Incontinence: A 16-Year Review", Am. J. Obstet. Gynecol., vol. 151, No. 2, pp. 224-226 (Jan. 15, 1985).

Morgan, J.E., M.D., "A sling operation, using Marlex Polypropylene mesh, for treatment of recurrent stress incontinence", Amer. J. Obstet. Gynecol., vol. 106, No. 3, pp. 369-377 (Feb. 15, 1970).

Narik, G., M.D. "A simplified sling operation suitable for routine use" Am. J. Obst. & Gynec., vol. 84, No 3, pp. 400-405 (Aug. 1, 1962).

Nichols, David H., MD, FACOG, "The Mersilene Mesh Gauze-Hammock for Severe Urinary Stress Incontinence" Obstetrics and Gynecology, vol. 41, No. 1, pp. 88-93 (Jan. 1973).

Nickel, Rafael F., et al., "Evaluation of a Transpelvic Sling Procedure With and Without Colposuspension for Treatment of Female Dogs With Refractory Urethral Sphincter Mechanism Incompetence" Veterinary Surgery, vol. 27, pp. 94-104, (1998), The American College of Veterinary Surgeons.

Norris, Jeffrey P., M.D., et al., "Use of Synthetic Material in Sling Surgery: A Minimally Invasive Approach" Journal of Endourology, vol. 10 No. 3, pp. 227-230 (Jun. 1996) Mary Ann Liebert, Inc.

O'Donnell, Pat D., M.D., "Combined Raz Urethral Suspension and McGuire Pubovaginal Sling for Treatment of Complicated Stress Urinary Incontinence" Journal of the Arkansas Medical Society, vol. 88, No. 8, pp. 389-392 (Jan. 1992).

Parra, R. O., et al., "Experience with a Simplified Technique for the Treatment of Female Stress Urinary Incontinence" British Journal of Urology, vol. 66, pp. 615-617 (1990).

Pelosi, Marco A., II, et al., "New Tranobturator Sling Reduces Risk of Injury" OBG Management, pp. 17-20, 30, 32, 35-38 (Jul. 2003).

Pelosi, Marco Antonio III et al., "Pubic Bone Suburethral Stabilization Sling: Laparoscopic Assessment of a Transvaginal Operation for the Treatment of Stress Urinary Incontinence" Journal of Laparoendoscopic & Advanced Surgical Techniques, vol. 9, No. 1 pp. 45-50 (1999).

Pereyra, Armand J et al, "Pubourethral Supports in Perspective: Modified Pereyra Procedure for Urinary Incontinence" Obstetrics and Gynecology, vol. 59, No. 5, pp. 643-648 (May 1982).

Pereyra, Armand J., M.D., F.A.C.S., "A Simplified Surgical Procedure for the Correction of Stress Incontinence in Women" West J. Surg. Obst. & Gynec. pp. 223-226 (Jul.-Aug. 1959).

Petros, P. E. Papa, "Medium-term Follow-up of the Intravaginal Slingplasty Operation Indicates Minimal Deterioration of Urinary Continence With Time" Aust NZ J Obstet Gynaecol, vol. 39, No. 3, pp. 354-356 (1999) (International Urogynecology Journal and Pelvic Floor Dysfunction, Reprinted from vol. 7, No. 3, pp. 133-137 (1996)).

Petros, P. E. Papa, "New Ambulatory Surgical Methods Using an Anatomical Classification of Urinary Dysfunction Improve Stress, Urge and Abnormal Emptying" Int-Urogynecol-J-Pelvic-Floor-Dysfunct, 8/5, pp. 270-277 (1997).

Petros, P. E. Papa, et al., "An analysis of rapid pad testing and the history for the diagnosis of stress incontinence" Acta Obstet Gynecol Scand 71, pp. 529-536 (1992).

Petros, P. E. Papa, et al., "An Anatomical Basis for Success and Failure of Female Incontinence Surgery" Scand J Urol Nephrol, Suppl. No. 153, pp. 55-60 (1993).

Petros, P. E. Papa, et al., "An integral theory of female urinary incontinence—Experimental and clinical considerations" Acta Obstet Gynecol Scand, vol. 69, Suppl. 153 pp. 7-31 (1990), The Scandinavian Association of Obstetricians and Gynecologists.

Petros, P. E. Papa, et al., "Anchoring the midurethra restores bladder-neck anatomy and continence" The Lancet, vol. 354, pp. 997-998 (Sep. 18, 1999).

Petros, P. E. Papa, et al., "Bladder Instability in Women: A Premature Activation of the Micturition Reflex" Neurourology and Urodynamics, vol. 12, pp. 235-238 (1993).

Petros, P. E. Papa, et al., "Cough Transmission Ratio: An Indicator of Suburethral Vaginal Wall Tension Rather Than Urethral Closure?" Acta Obstet Gynecol Scand, vol. 69 Suppl. 153, pp. 37-39 (1990).

Petros, P. E. Papa, et al., "Cure of Stress Incontinence by Repair of External Anal Spincter: Two Case Reports" Acta Obstet Gynecol Scand, vol. 69 Suppl. 153, p. 75 (1990).

Petros, P. E. Papa, et al., "Cure of Urge Incontinence by the Combined Intravaginal Sling and Tuck Operation" Acta Obstet Gynecol Scand, vol. 69 Suppl. 153, pp. 61-62 (1990).

Petros, P. E. Papa, et al., "Further Development of the Intravaginal Slingplasty Procedure—IVS III—(with midline tuck)" Scand J Urol Nephrol, Suppl. 153, pp. 69-71 (1993).

Petros, P. E. Papa, et al., "Non Stress Non Urge Female Urinary Incontinence—Diagnosis and Cure: A Preliminary Report" Acta Obstet Gynecol Scand, vol. 69 Suppl. 153. pp. 69-70 (1990).

Petros, P. E. Papa, et al., "Part I: Theoretical, Morphological, Radiographical Correlations and Clinical Perspective" Scand J Urol Nephrol, Suppl. 153. pp. 5-28 (1993).

Petros, P. E. Papa, et al., "Part II: The Biomechanics of Vaginal Tissue and Supporting Ligaments With Special Relevance to the Pathogenesis of Female Urinary Incontinence" Scand J Urol Nephrol, Suppl. No. 153, pp. 29-40 (1993).

Petros, P. E. Papa, et al., "Part III: Surgical Principles Deriving From the Theory" Scand J Urol Nephrol, Suppl. No. 53, pp. 41-52 (1993).

Petros, P. E. Papa, et al., "Part IV: Surgical Applications of the Theory—Development of the Intravaginal Sling Plasty (IVS) Procedure" Scand J Urol Nephrol, Suppl. No. 153, pp. 53-54 (1993).

Petros, P. E. Papa, et al., "Pregnancy Effects on the Intravaginal Sling Operation" Acta Obstet Gynecol Scand, vol. 69 Suppl. 153, pp. 77-79 (1990).

Petros, P. E. Papa, et al., "The Autogenic Ligament Procedure: A Technique for Planned Formation of an Artificial Neo-Ligament" Acta Obstet Gynecol Scand, vol. 69 Suppl 153, pp. 43-51 (1990).

Petros, P. E. Papa, et al., "The Combined Intravaginal Sling and Tuck Operation. An Ambulatory Procedure for Cure of Stress and Urge Incontinence" Acta Obstet Gynecol Scand, vol. 69 Suppl 153, pp. 53-59 (1990).

Petros, P. E. Papa, et al., "The Development of the Intravaginal Slingplasty Procedure: IVS II—with bilateral 'tucks')", Scand J Urol Nephrol, Suppl. 153. pp. 61-67 (1993).

Petros, P. E. Papa, et al., "The Free Graft Procedure for Cure of the Tethered Vagina Syndrome" Scand J Urol Nephrol, Suppl. No. 153, pp. 85-87 (1993).

Petros, P. E. Papa, et al., "The Further Development of the Intravaginal Slingplasty Procedure: IVS IV—(with "double-breasted" unattached vaginal flap repair and "free" vaginal tapes)" Scand J Urol Nephrol, Suppl. No. 153, pp. 73-79 (1993).

Petros, P. E. Papa, et al., "The Intravaginal Slingplasty Procedure: IVS VI—further development of the 'double-breasted' vaginal flap repair—attached flap" Scand J Urol Nephrol, Suppl. No. 153, pp. 81-84 (1993).

Petros, P. E. Papa, et al., "The Posterior Fornix Syndrome: A Multiple Symptom Complex of Pelvic Pain and Abnormal Urinary Symtoms Deriving From Laxity in the Posterior Fornix of Vagina" Scand J Urol Nephrol, Suppl. No. 153, pp. 89-93 (1993).

Petros, P. E. Papa, et al., "The Role of a Lax Posterior Vaginal Fornix in the Causation of Stress and Urgency Symptoms: A Preliminary Report" Acta Obstet Gynecol Scand, vol. 69 Suppl. 153, pp. 71-73 (1990).

Petros, P. E. Papa, et al., "The Tethered Vagina Syndrome, Post Surgical Incontinence and I-Plasty Operation for Cure" Acta Obstet Gynecol Scand, vol. 69 Suppl. 153, pp. 63-67 (1990).

Petros, P. E. Papa, et al., "The Tuck Procedure: A Simplified Vaginal Repair for Treatment of Female Urinary Incontinence" Acta Obstet Gynecol Scand, vol. 69 Suppl. 153, pp. 41-42 (1990).

Petros, P. E. Papa, et al., "Urethral Pressure Increase on Effort Originates From Within the Urethra, and Continence From Musculovaginal Closure" Neurourology and Urodynamics, vol. 14, pp. 337-350 (1995).

Petros, P. E. Pappa, "Development of Generic Models for Ambulatory Vaginal Surgery—Preliminary Report" International Urogynecology Journal, 9 pages (1998).

Pourdeyhimi, "Porosity of surgical mesh fabrics: New technology", J. Biomed. Mater. Res.: Applied Biomaterials, vol. 23, No. A1, pp. 145-152 (1989), ©1989 John Wiley & Sons, Inc.

Rackley, Raymond R., M.D., et al. "Tension-free Vaginal Tape and Percutaneous Vaginal Tape Sling Procedures" Techniques in Urology, vol. 7, No. 2, pp. 90-100 (2001).

Rackley, Raymond, M.D., "Synthetic slings: Five steps for successful placement" Urology Times, pp. 46, 48-49 (Jun. 2000).

Raz, Shlomo, et al., The Raz Bladder Neck Suspension Results in 206 Patients, The Journal of Urology, pp. 845-850 (Sep. 1992).

Raz, Shlomo, M.D. et al., "Female Urology—Second Edition" University of California at Los Angeles School of Medicine, articles pp. 80-86, 369-381, 382-391, 392-394, 395-398, 435-442, (1996) W.B. Saunders Company.

Raz, Shlomo, M.D., "Modified Bladder Neck Suspension for Female Stress Incontinence" Urology, vol. XVII, No. 1, pp. 82-85 (Jan. 1981) University of California Health Sciences Center, Los Angeles, CA.

Richardson, David A., M.D., et al., "Delayed Reaction to the Dacron Buttress Used in Urethropexy" The Journal of Reproductive Medicine, vol. 29 No. 9, pp. 689-692 (Sep. 1984).

Ridley, John H., M.D., "Appraisal of the Goebell-Frangenheim-Stoeckel sling procedure" Am. J. Obst. & Gynec. vol. 95, No. 5, pp. 714-721 (Jul. 1, 1966).

Roberts, Henry, M.D., M.R.C.O.G., "Cystourethrography in Women" Ethel Bovce University Fellowship vol. 25 No. 293, pp. 253-259 (May 1952) University of Liverpool.

Sloan, W. R., et al., "Stress Incontinence of Urine: A Retrospective Study of the Complications and Late Results of Simple Suprapubic Suburethral Fascial Slings" The Journal of Urology, vol. 110, pp. 533-536 (Nov. 1973).

Spencer, Julia R., et al., "A Comparison of Endoscopic Suspension of the Vesical Neck With Suprapubic Vesicourethropexy for Treatment of Stress Urinary Incontinence" The Journal of Urology, vol. 137, pp. 411-415 (Mar. 1987).

Stamey, Thomas A., M.D., "Endoscopic Suspension of the Vesical Neck for Urinary Incontinence in Females" Ann Surg., vol. 192, No. 4, pp. 465-471 (Oct. 1980).

Stanton, Stuart L., FRCS, FRCOG, "Suprapubic Approaches for Stress Incontinence in Women" JAGS, vol. 38, No. 3, pp. 348-351 (1990), The American Geriatrics Society.

Staskin, David R., et al., "The Gore-tex sling procedure for female sphincteric incontinence: indications, technique, and results" World J Urol., vol. 15, pp. 295-299 (1997) Springer-Verlag.

Studdiford, William E., M.D., "Transplantation of Abdominal Fascia for the Relief of Urinary Stress Incontinence" Am J Obst Gynec, vol. 47, pp. 764-775 (1944) Bellevue Hospital and New York University College of Medicine.

Ulmsten, U., "Female Urinary Incontinence—A Symptom, Not a Urodynamic Disease. Some Theoretical and Practical Aspects on the Diagnosis and Treatment of Female Urinary Incontinence" The International Urogynecology Journal, vol. 6, pp. 2-3 (1995).

Ulmsten, U., et al., "A Multicenter Study of Tension-Free Vaginal Tape (TVT) for Surgical Treatment of Stress Urinary Incontinence" The International Urogynecology Journal, vol. 9, pp. 210-213 (1998).

Ulmsten, U., et al., "A three-year follow up of tension free vaginal tape for surgical treatment of female stress urinary incontinence" The British Journal of Obstetrics and Gynaecology, vol. 106, pp. 345-350 (Apr. 1999).

Ulmsten, U., et al., "An Ambulatory Surgical Procedure Under Local Anesthesia for Treatment of Female Urinary Incontinence" The International Urogynecology Journal, vol. 7, pp. 81-86 (1996).

Ulmsten, U., et al., "Different Biochemical Composition of Connective Tissue in Continent and Stress Incontinent Women" Acta Obstet Gynecol Scand, vol. 66, pp. 455-457 (1987).

Ulmsten, U., et al., "Intravaginal Slingplasty (IVS): An Ambulatory Surgical Procedure for Treatment of Female Urinary Incontinence" Scand J Urol Nephrol,vol. 29, pp. 75-82 (1995) Scandinavian University Press.

Ulmsten, U., et al., "The unstable female urethra" Am. J. Obstet. Gynecol., vol. 144 No. 1, pp. 93-97 (1982).

Walters, Mark D., Percutaneous Suburethral Slings: State of the Art Presented at the conference of the American Urogynecologic Society, Chicago, 29 pages (Oct. 2001).

Waxman, Steve et al., Advanced Urologic Surgery for Urinary Incontinence, The Female Patient, vol. 21, pp. 93-100 (Mar. 1996).

Webster, George D., "Female Urinary Incontinence" Urologic Surgery—3rd Ed., Ch. 66, pp. 665-679 (1983).

Webster, George D., et al., "Voiding Dysfunction Following Cystourethropexy: Its Evaluation and Management" The Journal of Urology, vol. 144, pp. 670-673 (Sep. 1990) American Urological Association, Inc.

Winter, Chester C., M.D., "Peripubic Urethropexy for Urinary Stress Incontinence in Women" Urology vol. XX, No. 4, pp. 408-411 (Oct. 1982).

Woodside, Jeffrey R., et al., "Suprapubic Endoscopic Vesical Neck Suspension for the Management of Urinary Incontinence in Myelodysplastic Girls" The Journal of Urology, vol. 135, pp. 97-99 (Jan. 1986).

Zacharin, Robert F., "The suspensory mechanism of the female urethra" Journal of Anatomy, vol. 97, Part 3, pp. 423-427, (1963).

Zacharin, Robert F., FRCS, FRCOG, et al, "Pulsion Enterocele: Long-Term Results of an Abdominoperineal Technique" Obstetrics & Gynecology, vol. 55, No. 2, pp. 141-148 (Feb. 1980) The American College of Obstetricians & Gynecologists.

Zimmern, Phillippe E. at al , "Four-Corner Bladder Neck Suspension" Vaginal Surgery for the Urologist, vol. 2, No. 1, pp. 29-36 (Apr. 1994).

Declaration of Johann J. Neisz with Attachment (Mar. 19, 2004).

Bard, "Uretex Polypropylene Urethral Support—Safety, Simplicity, Flexibility" Marketing Material (2002) 8 pages.

Boston Scientific Corp., Boston Scientific Microvasive, "Precision Tack Transvaginal Anchor System—The Precise Approach to Transvaginal Sling Procedures" Marketing Material (1998) 4 pages.

Boston Scientific Corp., Boston Scientific Microvasive, "Precision Twist Transvaginal Anchor System—Low Profile Design for Precise Anchor Placement" Marketing Material (2000) 2 pages.

Boston Scientific Corp., "Advantage A/T—Surgical Mesh Sling Kit" Marketing Material (2002) 1 page.

Boston Scientific Corp., "Precision SpeedTac—Transvaginal Anchor System" Marketing Material (2002) 1 page.

Ethicon, Inc., TVT Tension-free Vaginal Tape, Gynecare, 23 pages (1999).

Qynecare TVT, "Tension-Free Support for Incontinence" Marketing Material, Gynecare Worldwide (Feb. 2002), 6 pages.

Gynecare, "TVT—Tension-Free Vaginal Tape, Minimally Invasive, Highly Effective Treatment for Female Stress Urinary Incontinence" Marketing Brochure, Ethicon, Inc. (1999) 6 pages.

Herniamesh USA Inc., "T-Sling (Totally Tension-free) Urinary Incontinence Procedure" Marketing Material (Jan. 2000), 2 pages.

Mentor, "The Strength of Suspend" Marketing Material (Mar. 2000) 6 pages.

Mentor, Sabre, "Generation Now" Marketing Material (May 2002) 4 pages.

Mentor, Sabre, Surgical Procedure, Marketing Material (Aug. 2002) 6 pages.

Mpaegntor-Porges, Trans-obturator tape, Le hamac perinial, Nos references, Marketing Material in French language (2003) 1 page.

Porges U.K. Ltd., "Uratape Perineal Hammock Urethral Support Tape—New Generation of Tape Perineal Implantation" Mentor, Marketing Material (2002) 4 pages.

Safyre, "The Essence of a Contemporary Synthetic Sling—Self-Anchoring Complete Adjustability Elastic" Promedon, Marketing Material (Jan. 30, 2002) 4 pages.

Urogynecology, Product Catalog, eg. SIS Technology, Bladder Suspension, Urodynamics and Urinary Diversion, Incontinence, Cook, Urological Inc. (1996) 36 pages.

Dietz, Hans, Md, et al., "Does the tension-free vaginal tape stay where you put it?" Am. J. Obstet Gynecol. V. 188, No. 4, pp. 950-953 (2003).

Drutz, H., et al., "Clinical and Urodynamic Re-evaluation of Combined Abdominal Marlex Sling Operations for Recurrent Stress Urinary Incontinence" Int. Urogynecol J. 1: pp. 70-73 (1990).

Fianu, Stefan, et al, Absorbable Polyglactin Mesh for Retropubic Sling Operations in Female Urinary Stress Incontinence, Gyneol. Obstet. Invest. 16, pp. 45-50 (1983).

Mentor-Porges, Come See Us at Booth #28, Marketing Material (Jul. 2002) 1 page.

Mouly, Patrick, et al., "Vaginal Reconstruction of a Complete Vaginal Prolapse: The Trans Obturator Repair" Journal of Urology, Apr. 2003, vol. 169 (4) supplement, p. 183, Abstract # V 702, AUA (Apr. 26-May 1, 2003) Chicago, IL.

Nicita, G. et al. "Six Year Results of Prosthetic Vaginal Surgery for Cystocele Repair" European Urology Supments 3 (2004) No. 2, p. 50 (Mar. 24-27 2004).

Ogundipe, Anthony, MD, et al., "Modified Suburethral Sling Procedure for Treatment of Recurrent or Severe Stress Urinary Incontinence" Surg. Gynecol. Obstet, V175, pp. 173-176 (Aug. 1992).

"Safyre and Transobturator", Video file on CD-ROM (2004).

Timmons, M. Chrystie, et al., "Abdominal Sacral Colpopexy in 163 Women with Posthysterectomy Vaginal Vault Prolapse and Enterocele—Evolution of Operative Techniques" J. of Reproductive Medicine, V.35, No. 4, pp. 323-327 (Apr. 1992).

"Vesica Sling Kits with Press-In Percutaneous Anchor System—Simplifying Sling Procedures" Marketing Material, Boston Scientific Corp., Boston Scientific Microvasive, (1998), 4 pages.

Young, Stephen B., et al., "The Mersilene mesh suburethral sling: A clincal and urodynamic evaluation" Am. J. Obstet. Gynecol. V. 173, pp. 1719-1726 (Dec. 1995).

* cited by examiner

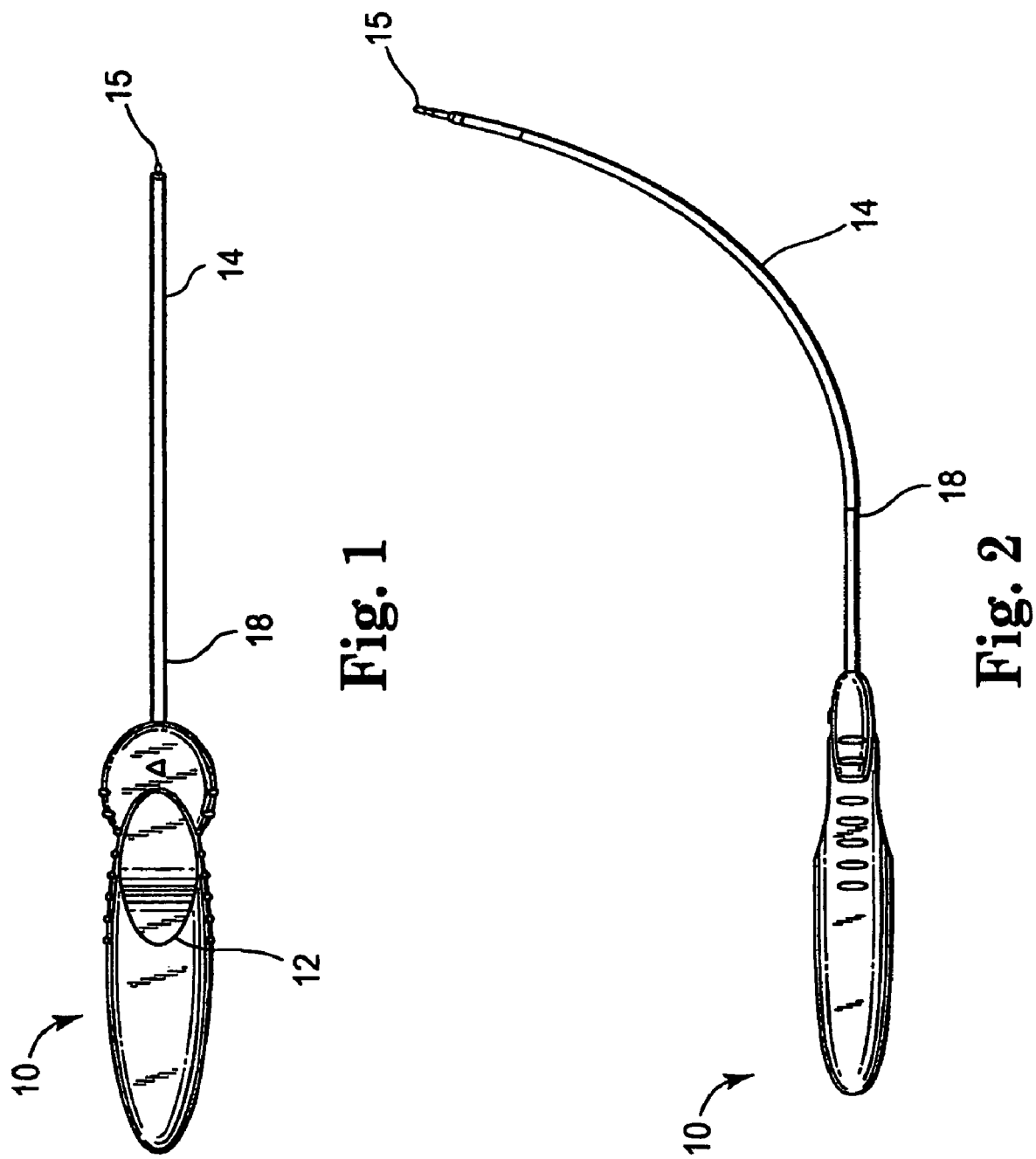

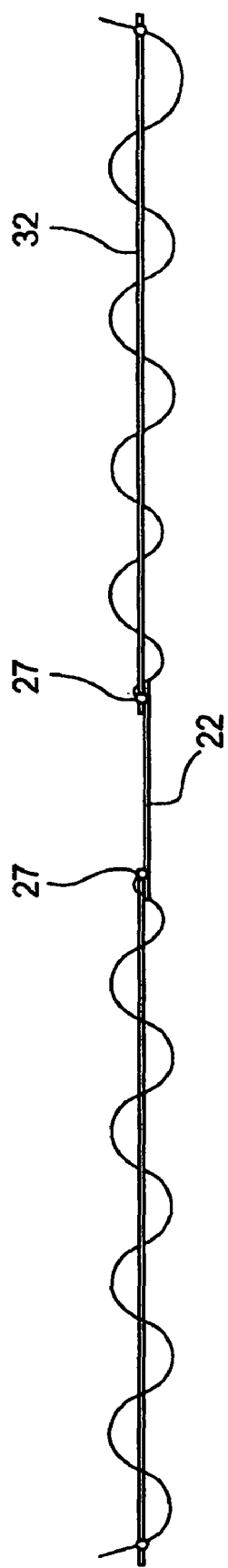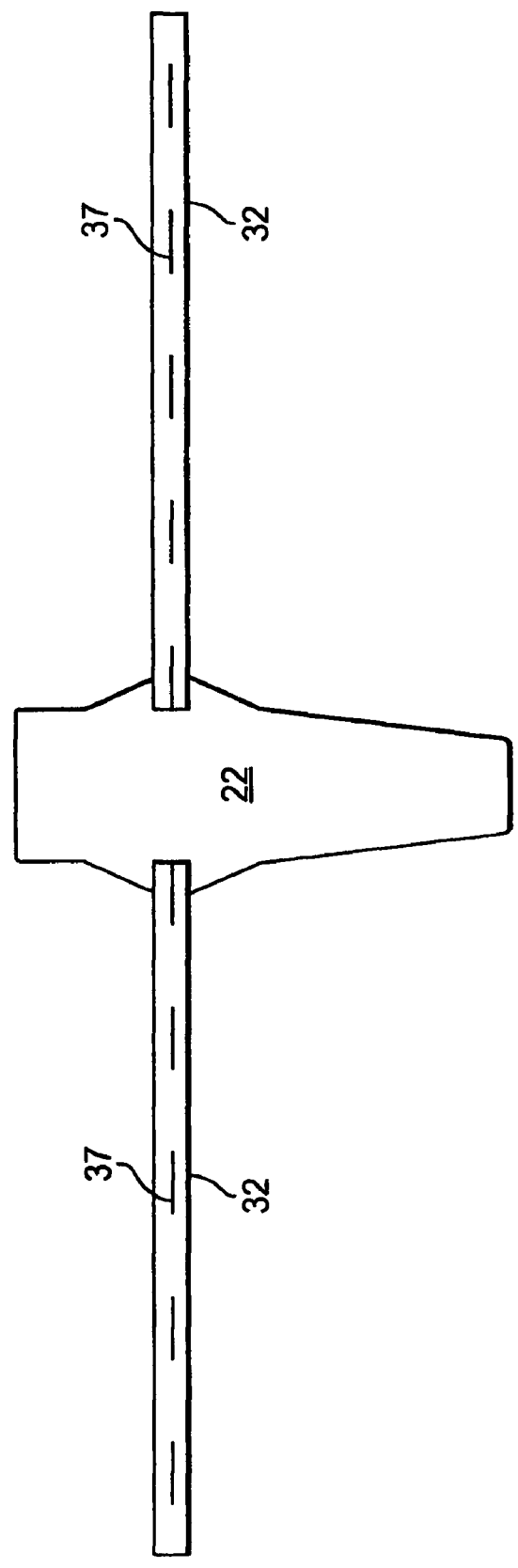

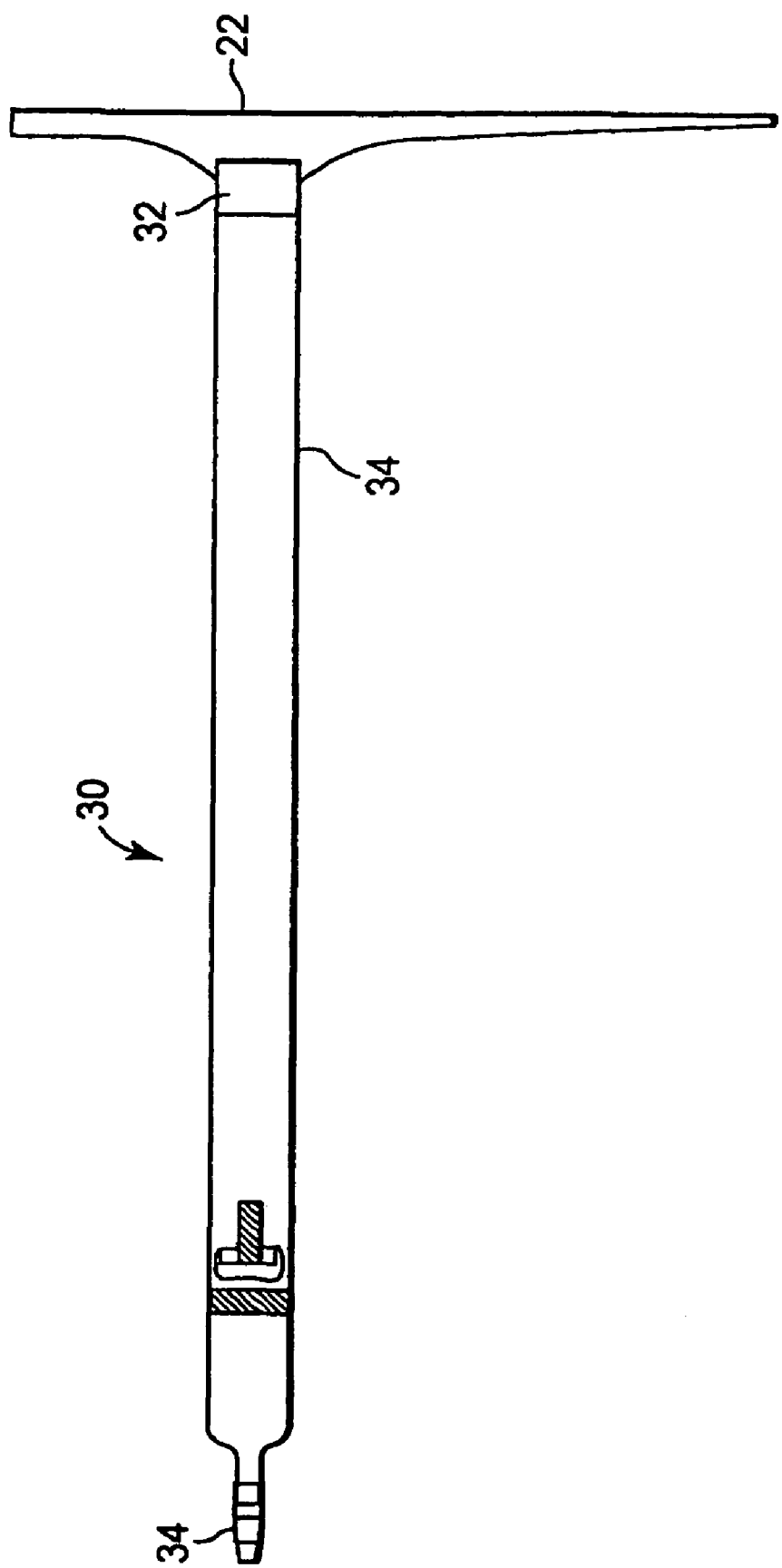

METHOD AND APPARATUS FOR TREATING PELVIC ORGAN PROLAPSE

PRIORITY

The present patent application is a continuation of U.S. Ser. No. 10/834,943, filed Apr. 30, 2004 now U.S. Pat. No. 7,500,945, wherein the entirety of said patent application is incorporated herein by reference.

BACKGROUND OF THE INVENTION

1. Field of the Invention
Urogenital Surgery
2. Description of the Related Art

Female genital prolapse has long plagued women. It is estimated by the U.S. National Center for Health Statistics that 247,000 operations for genital prolapse were performed in 1998. With the increasing age of the U.S. population, these problems will likely assume additional importance.

Vaginal prolapse develops when intra-abdominal pressure pushes the vagina outside the body. In a normal situation, the levator ani muscles close the pelvic floor. This results in little force being applied to the fascia and ligaments that support the genital organs. Increases in abdominal pressure, failure of the muscles to keep the pelvic floor closed, and damage to the ligaments and fascia all contribute to the development of prolapse. In addition, if a woman has a hysterectomy, the vaginal angle may be altered, causing increased pressure at a more acute angle, accelerating the prolapse.

There are generally two different types of tissue that make up the supportive structure of the vagina and uterus. First, there are fibrous connective tissues that attach these organs to the pelvic walls (cardinal and uterosacral ligaments; pubocervical and rectovaginal fascia). Second, the levator ani muscles close the pelvic floor so the organs can rest on the muscular shelf thereby provided. It is when damage to the muscles open the pelvic floor or during the trauma of childbirth that the fascia and ligaments are strained. Breaks in the fascia allow the wall of the vagina or cervix to prolapse downward.

Several factors have been implicated as being involved in genital prolapse in women. It is thought that individual women have differing inherent strength of the relevant connective tissue. Further, loss of connective tissue strength might be associated with damage at childbirth, deterioration with age, poor collagen repair mechanisms, and poor nutrition. Loss of muscle strength might be associated with neuromuscular damage during childbirth, neural damage from chronic straining, and metabolic diseases that affect muscle function. Other factors involved in prolapse include increased loads on the supportive system, as seen in prolonged lifting or chronic coughing from chronic pulmonary disease, or some disturbance in the balance of the structural support of the genital organs. Obesity, constipation, and a history of hysterectomy have also been implicated as possible factors.

The common clinical symptoms of vaginal prolapse are related to the fact that, following hysterectomy, the vagina is inappropriately serving the role of a structural layer between intra-abdominal pressure and atmospheric pressure. This pressure differential puts tension on the supporting structures of the vagina, causing a "dragging feeling" where the tissues connect to the pelvic wall or a sacral backache due to traction on the uterosacral ligaments. Exposure of the moist vaginal walls leads to a feeling of perineal wetness and can lead to ulceration of the exposed vaginal wall. Vaginal prolapse may also result in loss of urethral support due to displacement of the normal structural relationship, resulting in stress urinary incontinence. Certain disruptions of the normal structural relationships can result in urinary retention, as well. Stretching of the bladder base is associated with vaginal prolapse and can result in complaints of increased urinary urgency and frequency. Other symptoms, such as anal incontinence and related bowel symptoms, and sexual dysfunction are also frequently seen with vaginal prolapse.

Anterior vaginal wall prolapse causes the vaginal wall to fail to hold the bladder in place. This condition, in which the bladder sags or drops into the vagina, is termed a cystocele. There are two types of cystocele caused by anterior vaginal wall prolapse. Paravaginal defect is caused by weakness in the lateral supports (pubourethral ligaments and attachment of the bladder to the endopelvic fascia); central defect is caused by weakness in the central supports. There may also be a transverse defect, causing cystecele across the vagina.

Posterior vaginal wall prolapse results in descent of the rectum into the vagina, often termed a rectocele, or the presence of small intestine in a hernia sac between the rectum and vagina, called an enterocele. Broadly, there are four types based on suspected etiology. Congenital enteroceles are thought to occur because of failure of fusion or reopening of the fused peritoneal leaves down to the perineal body. Posthysterectomy vault prolapses may be "pulsion" types that are caused by pushing with increased intra-abdominal pressure. They may occur because of failure to reapproximate the superior aspects of the pubocervical fascia and the rectovaginal fascia at the time of surgery. Enteroceles that are associated with cystocele and rectocele may be from "traction" or pulling down of the vaginal vault by the prolapsing organs. Finally, iatrogenic prolapses may occur after a surgical procedure that changes the vaginal axis, such as certain surgical procedures for treatment of incontinence. With regard to rectoceles, low rectoceles may result from disruption of connective tissue supports in the distal posterior vaginal wall, perineal membrane, and perineal body. Mid-vaginal and high rectoceles may result from loss of lateral supports or defects in the rectovaginal septum. High rectoceles may result from loss of apical vaginal supports. Posterior or posthysterectomy enteroceles may accompany rectoceles.

As noted, vaginal prolapse and the concomitant anterior cystocele can lead to discomfort, urinary incontinence, and incomplete emptying of the bladder. Posterior vaginal prolapse may additionally cause defecatory problems, such as tenesmus and constipation.

Many techniques have been tried to correct or ameliorate the prolapse and its symptoms, with varying degrees of success. Nonsurgical treatment of prolapse involves measures to improve the factors associated with prolapse, including treating chronic cough, obesity, and constipation. Other nonsurgical treatments may include pelvic muscles exercises or supplementation with estrogen. These therapies may alleviate symptoms and prevent worsening, but the actual hernia will remain. Vaginal pessaries are the primary type of nonsurgical treatment, but there can be complications due to vaginal wall ulceration.

There are a variety of known surgical techniques for the treatment of anterior vaginal prolapses. In the small proportion of cases in which the prolapse is caused by a central defect, anterior colporrapphy is an option. This surgery involves a transvaginal approach in which plication sutures are used to reapproximate the attenuated tissue across the midline of the vagina. More commonly, the prolapse is due to a lateral defect or a combination of lateral and central defects. In these instances, several surgical techniques have been used, such as a combination of an anterior colporrapphy and a site-specific paravaginal repair. Both abdominal and vaginal approaches are utilized. Biological or synthetic grafts have been incorporated to augment repair.

Likewise, the treatment of posterior vaginal prolapses may vary. If symptoms are minimal, nonoperative therapy such as changes in activities, treatment of constipation, and Kegel exercises might be appropriate. Again, both vaginal and abdominal approaches are used, involving sutures to reapproximate the attenuated tissue and possibly a biological or synthetic graft to augment the repair.

Sacral colpopexy entails attaching vaginal vault to the sacrum by use of mesh or fascia. The surgery may be performed through an abdominal incision or laparoscopically. Complications include mesh infection, mesh erosion, bowel obstruction, and hemorrhage from the presacral venous complex. If synthetic mesh is used, it is typically carefully customized or assembled into a special shape by the surgeon. Sacral colpopexy can be a tedious, challenging surgical procedure, with an average procedure length of 247 minutes reported in Winters et al, *Abdominal Sacral Colpopexy and Abdominal Enterocele Repair in the Management of Vaginal Vault Prolapse*, Urology 56 (Suppl 6A) (2000): 55-63. Some of this time is attributed to the time required for the surgeon to fashion the implant. In addition, it is often required to correct multiple pelvic floor abnormalities simultaneously, further increasing surgical time.

Sacrospinous fixation is also used to treat vaginal vault prolapse. This procedure involves attaching the vaginal vault to the sacrospinous ligament. This procedure requires specialized skills and has the further disadvantage of tending to place the vagina in an artificial anatomical position.

Synthetic implants have been used to address pelvic organ prolapse and incontinence. Treatment of vaginal prolapse and treatment of incontinence are related in many ways. The two conditions are often associated with one another. Interestingly, relief of pelvic organ prolapse often results in incontinence in the patient.

Various sling procedures have been used. Commonly, a sling procedure is combined with an anterior colporhapphy. A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension sutures to a point of attachment (e.g. bone) through an abdominal and/or vaginal incision. Examples of sling procedures are disclosed in U.S. Pat. Nos. 5,112,344; 5,611,515; 5,842,478; 5,860,425; 5,899,909; 6,039,686, 6,042,534 and 6,110,101.

Although serious complications associated with sling procedures are infrequent, they do occur. Complications include urethral obstruction, development of de novo urge incontinence, hemorrhage, prolonged urinary retention, infection, and damage to surrounding tissue and sling erosion.

The TVT Tension-free Vaginal Tape procedure utilizes a Prolene™ nonabsorbable, polypropylene mesh to treat incontinence. A plastic sheath surrounds the mesh and is used to insert the mesh. Abdominal and vaginal incisions are made, followed by implantation of the mesh using two curved, needle-like elements to push the mesh through the vaginal incision and into the paraurethral space. Using the procedure described elsewhere, the mesh is looped beneath the bladder neck or urethra. The sling is positioned to provide appropriate support to the bladder neck or urethra. When the TVT mesh is properly positioned, the cross section of the mesh should be substantially flat. In this condition, the edges of the mesh do not significantly damage tissue.

Complications associated with the TVT procedure and other known sling procedures include injury to blood vessels of the pelvic sidewall and abdominal wall, hematomas, urinary retention, and bladder and bowel injury due to passage of large needles. One serious disadvantage of the TVT procedure, particularly for surgeons unfamiliar with the surgical method, is the lack of information concerning the precise location of the needle tip relative to adjacent pelvic anatomy. If the needle tip is allowed to accidentally pass across the surface of any blood vessel, lymphatic duct, nerve, nerve bundle or organ, serious complications can arise. These shortcomings, attempts to address these shortcomings and other problems associated with the TVT procedure are disclosed in PCT publication nos. PCT WO 00/74613 and PCT WO 00/74594.

Additional problems are associated with the TVT and other sling procedures. Due to the tough fibrous nature of fascia and muscle tissues, forceps or similar instruments are needed to withdraw the needles through the abdominal wall. However, the smooth surface of the needles, which facilitates insertion through the tissues, prevents secure attachment of the forceps onto the needles, causing slippage or detachment of the forceps during the withdrawal procedure. Improper placement of the TVT mesh is also particularly troublesome. If the mesh is too loosely associated with its intended physiological environment, the mesh may be ineffective in supporting the urethra and treating incontinence. Several complications can arise from a mesh that is too tightly placed including retention, sling erosion and other damage to surrounding tissue such as the urethra and vagina. Surgeons may exacerbate these problems by improperly attempting to adjust the tension of a sling. If insufficient adjustment force is applied, the sling will simply exhibit a memory property and return to its original, unacceptable position. As a result, surgeons are tempted to use a great deal of force in order to loosen a sling that is perceived to be too tightly associated with its intended physiological environment. If excessive force is applied, the mesh will plastically deform and the cross section of the mesh will become arcuate. Excessive deformation may result in a lack of efficacy or, even worse, the edges of the mesh may curl up and present a relatively sharp, frayed surface. In this curled or deformed state, the edges of the TVT mesh present sharp surfaces that can readily abrade or otherwise damage adjacent tissue such as the urethra, bladder or vagina. The problems associated with the TVT mesh device are commonly seen in other similar sling or synthetic implant devices.

U.S. Pat. No. 6,695,855 (Gaston) describes a device for treating a prolapse by vaginal suspension. The device includes an elongate, flexible pierced material, a suture connected to the material, and a suture needle joined to the suture. The device is long enough to enable posterior suspension of the vagina at the front part of the sacrum. The other end of the device includes a distal portion having a width such that it can cover at least a large part of the posterior part of the vagina, a rounded cut-out with dimensions that enable it to be engaged around the base of the vagina on at least a large part of the lower half of the wall of the vagina. The suture is connected to the article so that it is offset sidewise in relation to the cut-out.

PCT Publication No. WO 00/27304 (Ory) discloses a suspension device for treating prolapse and urinary incontinence. The device comprises at least one filiform suspension cord with limited elasticity and at least two anchoring parts linked to the ends of the cord.

U.S. Pat. No. 5,112,344 and PCT Publication No. PCT/US02/32284 disclose surgical devices for female pelvic health procedures. The IVS Tunneller device (available from U.S. Surgical, Norwalk, Conn.) comprises a fixed delta wing handle, a hollow metal tube, and a stylet that is placeable within the tube. The stylet has a rounded plastic tip on one end and an eyelet on the other end. The device may be used to implant a polypropylene tape for infracoccygeal sacropexy and other surgical procedures.

A single rigid, hollow, metal tube is associated with the IVS Tunneller device. This tube passes through two separate regions of the patient's body with the attendant risk of cross-contamination. The outer diameter is also relatively large (about 0.25 inches) with the attendant risk of tissue damage due to such large diameter.

The polypropylene tape supplied with the IVS Tunneller is of a thin, rectangular shape and approximately 8 mm by 350 mm. This tape is not believed to be optimally sized and shaped to afford concomitant procedures such as enterocele, cystocele, and or rectocele repairs. The tape is also largely inextensible. It is highly resistant to elongation under a longitudinal force. Such inextensibility is believed to be associated with higher risk of tissue erosion and failure.

There is a desire to obtain a minimally invasive yet highly effective device and method that can be used to treat pelvic organ prolapse with minimal to no side effects. Such a device should reduce the complexity of the currently available procedures, be biocompatible, adjustable, and non-toxic. The treatment methods using the device should reduce pain, operative risks, infections and post operative hospital stays. Further, the method of treatment should also improve the quality of life for patients.

SUMMARY OF THE INVENTION

The present invention is directed to a method and apparatus for treating pelvic organ prolapse, and a kit containing elements for practicing the same. The present invention includes a support member less susceptible to deformation, relative to the prior art, following implantation and a means for repositioning and adjusting the support member which does not subject the sling to deformation pressures. The method of treatment is one that allows the operator to know the location of the instruments, as final passage of the needle is aided by the operator's use of his finger, making the method less risky for the patient. The apparatus and method is convenient for the operator, in that the apparatus is relatively simple to operate and contained within the described kit. The sling portion is relatively extensible compared to the prior art. The needle is of a small diameter to reduce the risk of trauma.

The method for repairing pelvic organ prolapse in a patient generally includes the steps of establishing a first pathway between the external perirectal region of the patient and the region of the ischial spine space in tissue on one side of the prolapsed organ, and establishing a second pathway in tissue on the contralateral side of the prolapsed organ. A support member including a central support portion and two end portions is positioned beneath the prolapsed organ in such a way as to allow repositioning of the organ into its anatomically appropriate location. The end portions of the support member are introduced through the respective tissue pathways. The end portions are adjusted so that the support member is located in a therapeutic relationship to the prolapsed organ that is to be supported.

In one embodiment of the invention, the method is directed to treatment of posterior vaginal prolapse. In other embodiments, the method is directed to treatment of vaginal vault prolapse, enterocele, rectocele, or a combination of more than one of these conditions. In another embodiment, the step of establishing the two tissue pathways between the external perirectal region and the region of the ischial spine of the patient, includes the steps of making a midline incision across the vagina to create access to the region of the ischial spine, through sharp and blunt dissection, and making an incision lateral and posterior to the rectum in the skin of a buttocks. A needle is passed from the incision lateral and posterior to the rectum toward the vaginal incision. The tip of the needle is palpated distal and inferior to the ischial spine and then passed through the coccygeous muscle. This step is performed on a first side, then on the contralateral side.

Further, in another embodiment, the step of positioning a support member in a position to support the prolapsed organ in its anatomically correct position includes the step of connecting the support member to the tip of the passed needle, as disclosed in U.S. Pat. No. 6,652,450, which is incorporated by reference. The step of introducing the end portions through the tissue pathways includes the step of retracting back through the respective pathways a needle to which the end portions have been connected. The step of adjusting the end portions so that the support member is in a therapeutic relationship to the prolapsed vagina that is to be supported further includes the steps of attaching the support member to the vaginal wall with sutures, ensuring the vaginal vault is in an appropriate anatomical position, and adjusting the support member by manipulation of the end portions.

The present invention further provides an apparatus for treatment of pelvic organ prolapse. The apparatus broadly includes a support portion with two ends, for placement in a therapeutically effective position, and two elongated end portions connected respectively to each end of the support portion.

In one embodiment of the invention, the apparatus includes repositioning means for effecting tightening or loosening of the apparatus without adversely affecting its therapeutic efficacy. According to an embodiment, the repositioning means includes at least one filament threaded along at least one end portion. The repositioning means may include at least one removable plastic sheath on at least one end portion, wherein the sheath is configured to affect tightening of the apparatus when the apparatus is partially implanted and the sheath is removed.

In one embodiment, the support portion of the apparatus is substantially rectangular, with two long sides and two short sides. The end portions are connected to the first and second long sides, respectively.

In another embodiment, the apparatus is substantially one tape, in which the support portion is a wider center section, relative to the two end portions, in which the support portion and the end portions are substantially one tape. Such an embodiment would allow for easier and more secure suture attachment.

In another embodiment, the support portion is of a different material in order to provide for better suture retention.

In another embodiment, the support portion of the apparatus includes first and second elongated portions and means for inserting and securing a biological graft material between the first and second elongated portions.

In another embodiment, the support portion of the apparatus is made from a polypropylene monofilament mesh. At least one of the end portions is made from a polypropylene monofilament mesh according to one embodiment.

In one embodiment, at least one of the end portions of the support member includes a connector configured to attach securely with the end of the needle.

The present invention also provides a kit including the elements for practice of the present method. The kit broadly includes a means for repositioning and supporting the prolapsed organ in a physiologically correct position and a means for attaching said repositioning and supporting means to an appropriate anatomical structure.

In another embodiment, the kit of the present invention includes a support member including a support portion and two end portions, wherein at least one end portion includes a removable plastic sheath, first and second needles configured to atraumatically form first and second pathways through tissue adjacent to the prolapsed organ, respectively, and handles for directing the needles.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a top view of a needle with a handle;

FIG. 2 is a side perspective of a needle with a handle;

FIG. 5 is a side view of the support member showing a filament tension control member;

FIG. 6 is a top view of an embodiment of the support member showing a filament tension control member;

FIG. 7 is a side perspective of the support member combined with a sheath and a dilator.

DETAILED DESCRIPTION OF THE PREFERRED EMBODIMENTS

Figure 3:
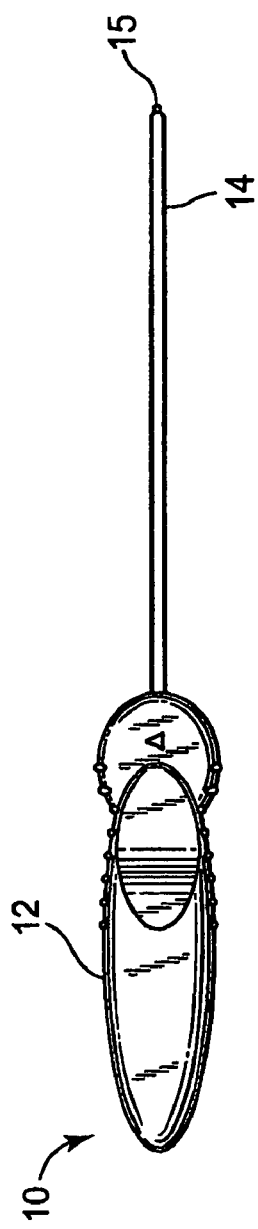
FIG. 3 is another top view of a needle with a handle.

Referring now to the drawings, wherein like reference numerals designate identical or corresponding parts throughout the several views. The following description is meant to be illustrative only and not limiting. Other embodiments of this invention will be apparent to those of ordinary skill in the art in view of this description.

Two tissue pathways are established between the external perirectal region and the region of the ischial spine of the patient. These pathways are made by making incisions in the rectal area and the vaginal apex and passing a needle through the rectal area incision toward the vaginal incision. Referring now to the drawings, wherein like reference numerals designate identical or corresponding parts throughout the several views, FIG. 1 shows a needle 14 and handle 10 suitable for use in the present invention. The handle 10 can be any suitable handle known in the art. U.S. Pat. No. 6,652,450, hereby incorporated by reference in its entirety, discloses several possible configurations. The needle 14 is generally curved or arcuate. A variety of needle designs and/or configurations may be used including, without limitation, straight, bent, curved, arc-shaped, Stamey, Raz and other configurations, all references hereinafter will be made to an arc-shaped needle in the spirit of brevity and reader convenience. Further, U.S. Pat. No. 6,652,450 discloses multiple acceptable configurations, and is hereby incorporated by reference.

Overall, the shape of the needle 14 should facilitate and provide controlled passage of the needle 14 through tissue as required. The ends or tip of the needle 14 are generally not sharpened, but may be tapered to afford easy passage through tissue while providing a blunt surface that avoids cutting sensitive tissue such as the bowel. It is preferred that the diameter of the needle 14 be small relative to the prior art to reduce tissue trauma.

The needle 14 is made of a malleable, yet durable, biocompatible surgical instrument materials such as, but not limited to, stainless steel, titanium, Nitinol, polymers, plastics and other materials, including combinations of materials. The needle 14 should have sufficient structural integrity to withstand the various forces (e.g. forces caused by dilator attachment, cystoscopy aid passage, and penetration/passage of the needle 14 through the various tissues) without undergoing any significant structural deformation. Optionally, the needles 14 could be sufficiently malleable to allow a practitioner or user of the device to modify the needle 14 to a desired shape and, thereby, optimize the procedural approach.

FIG. 1 shows a needle tip 15. The needle tip is optionally adapted to connect securely to a connector on the end of a sheath associated with at least one of the end portions of the support member. Many different configurations of such a system are known in the art and within the scope of the present invention. Several are disclosed in U.S. Pat. No. 6,652,450, which is incorporated by reference.

Following passage through the pathways, the needle tip is connected to a support member of the present invention. Following proper positioning of the support member, the needles are retracted back through the skin incision, carrying the end portions of the support member to the skin incision. FIG. 6 shows an embodiment of the support member of the present invention. The support member is a mesh tape including the support portion 22 and two end portions 32. In various embodiments of the invention, the support member may be a one piece mesh with the support portion substantially continuous with the end portions. In the illustrated embodiment of FIG. 6, the support portion is a larger substantially rectangular mesh that is provided pre-attached to the tape.

Many different types of mesh are known in the art and may be suitable for the present invention. Both biocompatible absorbable and non-absorbable yarns can be used to make the surgical meshes required. Suitable non-absorbable materials for use in the present invention include, but are not limited to, cotton, linen, silk, polyamides (polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terephthalate, copolymers and blends thereof), fluoropolymers (e.g. polytetrafluoroethylene and polyvinylidene fluoride) polyolefins (e.g. polypropylene including isotactic and syndiotactic polypropylene and blends thereof, as well as, blends composed predominately of isotactic or syndiotactic polypropylene blended with heterotactic polypropylene (such as are described in U.S. Pat. No. 4,557,264 issued Dec. 10, 1985 assigned to Ethicon, Inc. hereby incorporated by reference) and polyethylene (such as is described in U.S. Pat. No. 4,557,264 issued Dec. 10, 1985 assigned to Ethicon, Inc. hereby incorporated by reference)) and combinations thereof Suitable absorbable materials for use as yarns include but are not limited to aliphatic polyesters which include but are not limited to homopolymers and copolymers of lactide (which includes lactic acid d-,l- and meso lactide), glycolide (including glycolic acid), .epsilon.-caprolactone, p-dioxanone (1,4-dioxan-2-one), trimethylene carbonate (1,3-dioxan-2-one), alkyl derivatives of trimethylene carbonate, delta.-valerolactone, .beta.-butyrolactone, .gamma.-butyrolactone, .epsilon.-decalactone, hydroxybutyrate, hydroxyvalerate, 1,4-dioxepan-2-one (including its dimer 1,5,8,12-tetraoxacyclotetradecane-7, 14-dione), 1,5-dioxepan-2-one, 6,6-dimethyl-1,4-dioxan-2-one and polymer blends thereof.

In the present invention, the mesh is preferably fabricated from a 4.0 mil diameter monofilament polypropylene yarn by employing methods known in the art and described in "Warp Knitting Production" by Dr. S. Raz, Melliand Textilberichte GmbH, Rohrbacher Str. 76, D-6900 Heidelberg, Germany (1987), the contents of which are incorporated by reference herein. U.S. Pat. No. 6,638,284 is also herein incorporated by reference in its entirety.

A preferred mesh for use in the present invention is a polypropylene mesh possessing a thickness of about 0.021 inches, has about 27.5 courses per inch, and 13 wales per inch. It has three bar warp knit construction with a bar pattern set-up of #1: 1/0, 2/3, 2/1, 2/3, 1/0, 1/2, 1/0, 1/2: #2: 1/0, 2/3, 2/3, 1/0: #3: 2/3, 1/0, 1/2, 1/0, 2/3, 2/1, 2/3, 2/1.

In an embodiment, the apparatus of the present invention can have different mesh knits in the support member and the end portions. Such a construction would allow use of the optimum knit for support or anchoring. Such an apparatus could be manufactured by use of variable knitting and/or variable heat-setting techniques.

FIG. 6 also illustrates the tension control member. The tension control member serves as a repositioning means to effect tightening or loosening of the apparatus without adversely affecting the therapeutic efficacy of the apparatus.

Several different embodiments of tension adjustment member are within the scope of the present invention. In the illustrated embodiment, a tension control member is a monofilament fiber woven into the support member and attached to the support member via attachment points 27 located near the support portion 22 of the support member.

Other attachment configurations for the tension control member are also included within the scope of the claimed invention. Several variations of the tension control member are described in U.S. Pat. No. 6,652,450, which is incorporated by reference in its entirety.

The tension control member enables surgeons to easily tighten or loosen the support member tension during the surgical procedure. To reduce the tension of the support member using the tension control member, the surgeon contacts the support member and tension control member adjacent the prolapsed organ and pulls away from the organ. The tension of the central portion may be increased by grasping the support member and tension control member above the vaginal incision and pulling upward. One or both end portions of the support member and tension control member may be grasped to increase the tension of the support member, effecting tightening by pulling the end portions out at the incisions in the buttocks. Affording adjustment of the support member facilitates proper support member placement and helps avoid complications such as recurrence and tissue erosion arising out of improper placement.

The individual fibers or filaments comprising the tension control member may be extruded, woven, braided, spun, knitted, non-woven or have other similar configurations. Tension control member properties, such as tensile strength, elongation at break point, stiffness, surface finish, etc., may be similar to or different from those of the support member and may vary along the length of the support member.

Figure 4:
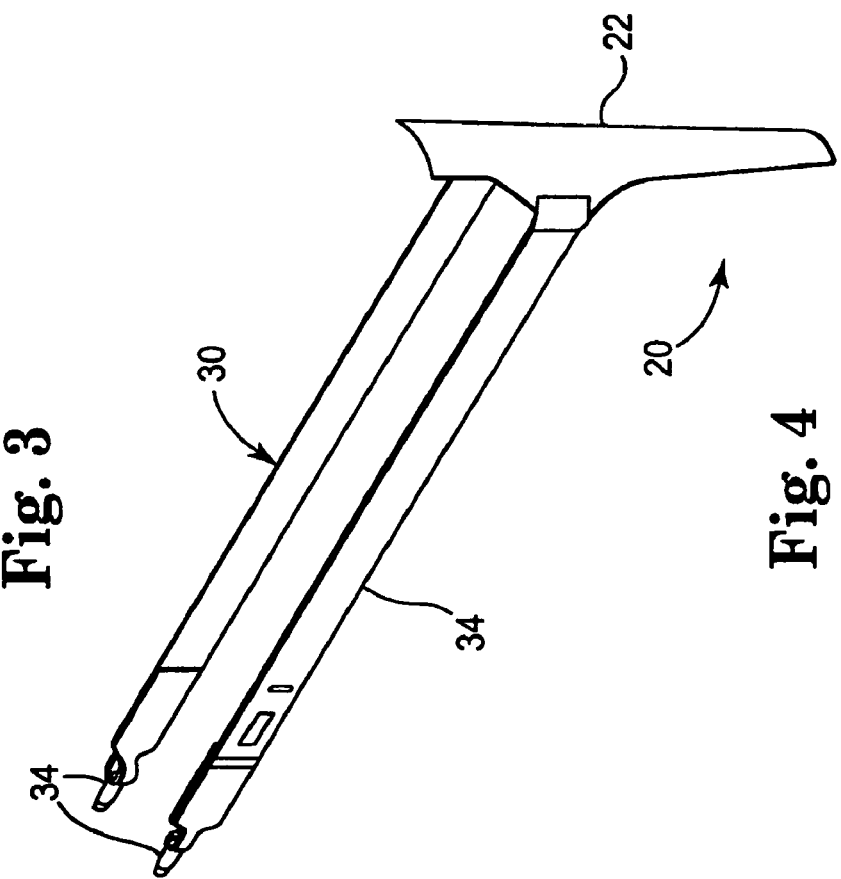
FIG. 4 is a perspective view of the support member combined with a sheath and a dilator.

FIGS. 4 and 7 show a mesh/sheath assembly. In this preferred embodiment, the end portions 32 of the support member are substantially enclosed by a sheath 34. The sheath acts to ease the passage of the mesh end portions 32 through the tissue and to protect the mesh from deformation. The sheath 34 further serves to maintain the mesh in a more sterile condition because, prior to removal of the sheath, the mesh itself has not contacted the vagina. The sheath 34 further provides a means of adjusting the positioning of the support member through manual manipulation of the sheath 34 before their removal. The sheath 34 may optionally further comprise a connecting mechanism to affect a secure attachment to the end of the needle. Such mechanism may be one of many different configurations known in the art, such as those keying configurations disclosed in U.S. Pat. No. 6,652,450, which is incorporated by reference. A preferred embodiment comprises a loop for attachment of the end portions to the needle. This loop is enlarged to allow a surgeon to place his finger through the loop and push the connector onto the needle.

Numerous modifications and variations of the present invention are possible in light of the above teachings. It is understood that within the scope of the appended claims, the invention may be practiced other than as specifically described herein.

EXAMPLE OF METHOD

While many methods are contemplated herein, an example use of the method and apparatus of treating pelvic organ prolapse is disclosed, referring to FIGS. 9 through 25.

The procedure can be carried out under local or general anesthesia. An incision is made midline across the vaginal apex with shapr and blunt dissection to the ischial spine. Two small incisions are also made in the skin of the buttocks. Needles are passed from perianal skin incisions in the buttocks to the vaginal incision. The needle tip is palpated distal and inferior to the ischial spine prior to passage through the coccygeus muscle. Further dissection may be desired to aid palpation of the needle passage. Connectors are connected to each needle end. Needles are retracted and mesh is positioned. The mesh is then attached to the vaginal vault, tensioned, and the incisions are closed.

One embodiment of the present invention is a sterile, single use product consisting of two stainless steel curved needles and a polypropylene mesh implant. The same polypropylene mesh is available in an alternative configuration that allows the attachment of biological material.

Locking connectors on the ends of the mesh attach to each needle tip and are used to hold the mesh secure to the needle during passage of the mesh through the body. Once snapped onto the needle tip, the connectors cannot be removed.

Three main preferred embodiments of the present apparatus are herein described. The physician may decide at his/her discretion which configuration is most appropriate for a particular patient.

A first embodiment (described herein as the tape embodiment) includes one-piece self-fixating mesh, two removable plastic insertion sheaths over the mesh, and two locking connectors attached to the insertion sheaths. The tape is knitted polypropylene monofilament mesh that is pre-cut to 1.1 cm width×50 cm length with a non-absorbable or absorbable tensioning suture (polypropylene) threaded through the length to allow for tensioning adjustment after placement. The sheath affords convenient travel of the mesh through the tissue. Finger loops are formed by the sheath to allow for easy attachment of the connectors to the needle tips. The synthetic mesh tape is intended to remain in the body as a permanent implant.

A second embodiment (described herein as the cape embodiment) adds a 4 cm×13 cm mesh to the tape. This soft knitted mesh has large pores and is also made of Polypropylene. The mesh is pre-attached to the tape and can be trimmed to suit surgical preference.

A third embodiment (described herein as the bio-cape embodiment) consists of two separate 1.1 cm×22 cm polypropylene mesh pieces, using the same material as in the tape version. However, one end has a locking connector and finger loop and the other end has a plastic clamp attached to a Y-shaped mesh used to facilitate attachment to a biological implant. The clamp is designed to facilitate the attachment of graft material with sutures In order to use the present invention in treatment of pelvic organ prolapse, the patient should initially be prepared by placing the patient in a modified dorsal lithotomy position with hips flexed, legs elevated in stirrups, and buttocks even with the edge of the table. Vaginal retraction may be used, if desired. Palpate the location of the ischial spines.

Figure 8:
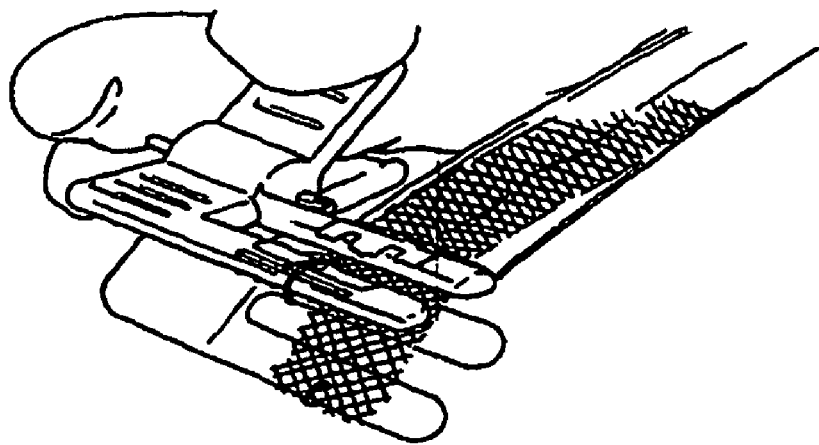
FIGS. 8 through 19 illustrate the mechanism for attaching a biological graft to the present invention.
Figure 9:
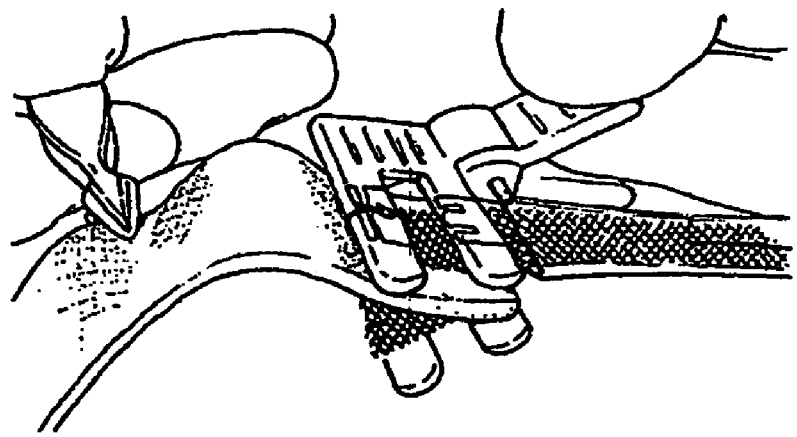
Figure 10:
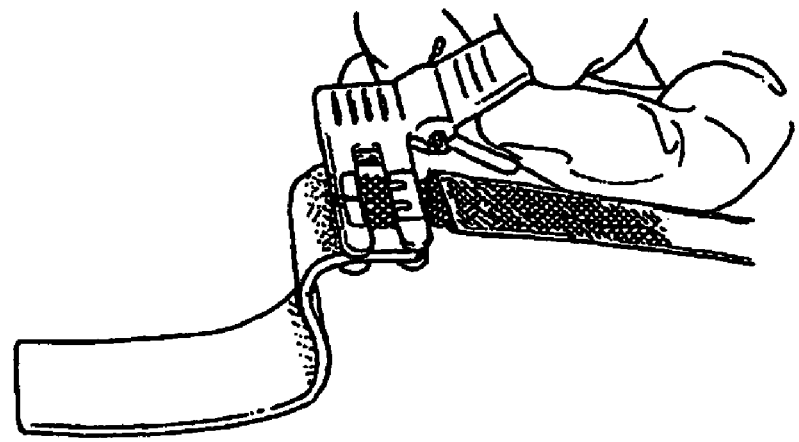
Figure 11:
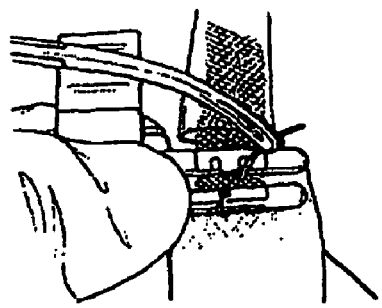
Figure 12:
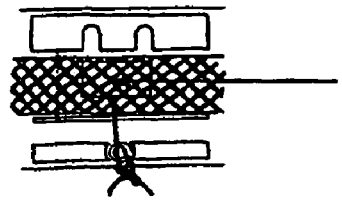
Figure 13:
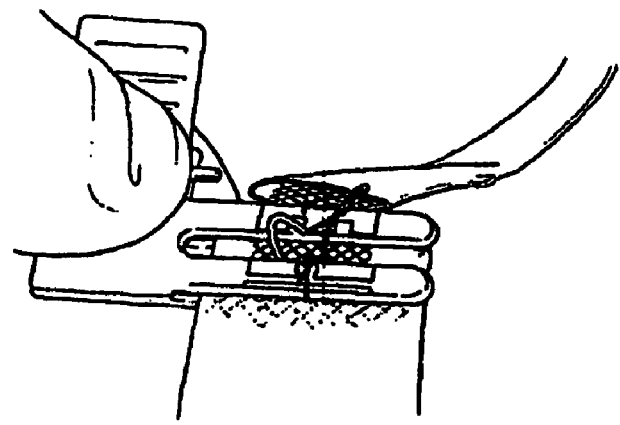
Figure 14:
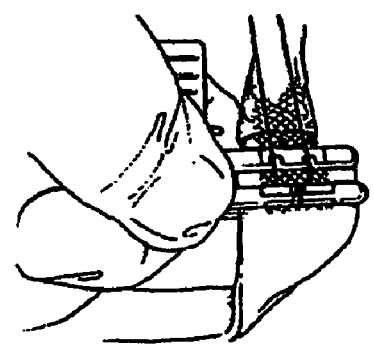
Figure 15:
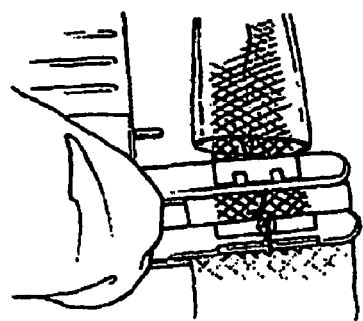
Figure 16:
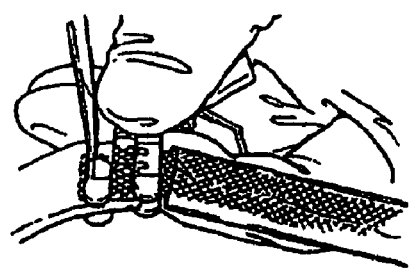
Figure 17:
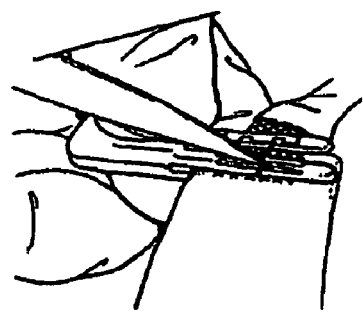
Figure 18:
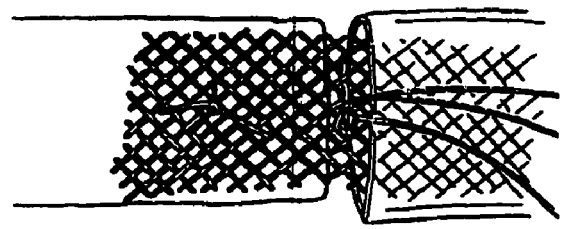
Figure 19:
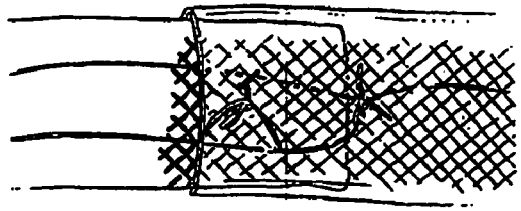

The various embodiments require differing product preparations. If the tape embodiment is selected, no further preparation is required. If the cape embodiment is selected, trim the rectangular mesh attachment to the desired size and shape. If the bio-cape embodiment is selected, several steps are required to prepare the product. First, remove the biological graft from its package and prepare it as needed. Second, trim the biological graft to the desired size and shape. Third, squeeze the clamp to separate the mesh tape, as shown in FIG. 8. Fourth, insert graft material into open clamp using printed marks on the device as guides to the center of the graft, as shown in FIG. 9. Fifth, release clamp to secure the graft material, as shown in FIG. 10. Sixth, with desired suture, pass up through the clamp, as shown in FIGS. 11 and 12. Seventh, pass suture down through the clamp, as shown in FIG. 13. Eighth, secure the passed sutures using the surgeon's knot(s) of choice, making additional throws if needed, as shown in FIGS. 14 and 15. Ninth, cut clamp sutures by passing scissors or scalpel down each side of the clamp, as shown in FIGS. 16 and 17. Tenth, remove clamp. The clamp attachment sutures remain with the clamp, as shown in FIG. 18. Eleventh, assess attachment of the graft material to the mesh tape. Twelfth, slide protective sheath over mesh connection to aid deployment, as shown in FIG. 19. Repeat attachment steps on the opposite side of the graft.

Following any required preparation, the procedure is the same for all three of the preferred embodiments:

(1) Gain access to the external vaginal vault using surgeon's preferred method of incision and dissection. If the cape is used, complete rectovaginal dissection is required.

Figure 20:
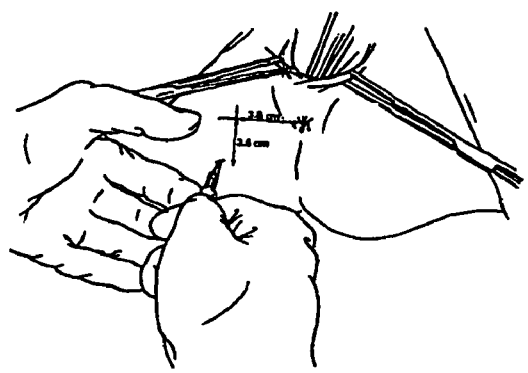
FIG. 20 illustrates the positioning of external incisions on the rectum of the patient.

(2) Make two small stab incisions on each side of the rectum approximately 3 cm lateral and 3 cm posterior to the anus, as shown in FIG. 20.

(3) Grasp the needle in one hand with the needle tip between the thumb and forefinger. Place the other hand near the needle bend. The two needles are identical. Either side may be done first.

Figure 21:
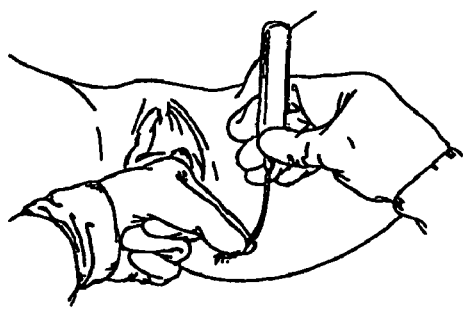
FIG. 21 illustrates a method of inserting the needle in a patient.

(4) Point the needle tip perpendicular to the skin with the handle pointing upward in a 12:00 position, as shown in FIG. 21.

(5) Direct the needle at a slight upward and lateral angle through the buttock. Puncture the initial layers of tissue by pushing on the needle bend until the needle enters the ischiorectal fossa.

Figure 22:
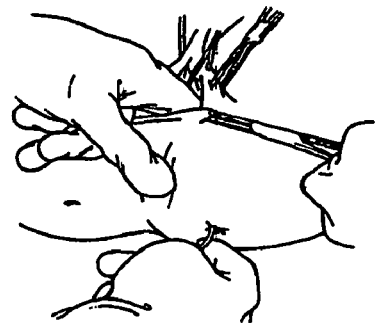
FIG. 22 illustrates palpation to aid passage of the needle to its appropriate position.

(6) Continue to pass the needle tip lateral and parallel to the rectum toward the ischial spine. Palpate as needed, as shown in FIG. 22.

(7) Palpate the needle tip in front of the ischial spine. Penetrate the levator muscle advancing and lightly turning the needle tip medially toward the vaginal vault.

(8) Perform digital rectal exam to verify rectal integrity.

(9) Repeat steps 3-9 on patient's contralateral side.

Figure 23:
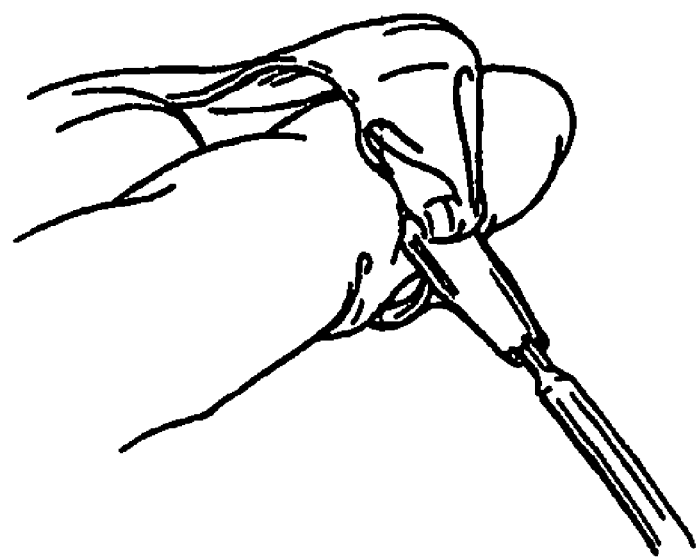
FIG. 23 illustrates an embodiment of the connector on the end portion of the mesh.

(10) Insert a finger into the loop behind the connector on the mesh, as shown in FIG. 23. Insert the connector into the vagina. Snap onto the needle tip.

(11) Pull each needle and connector back through the skin incision. Adjust the sheath and mesh into an approximate position.

(12) Cut the needles from the mesh near the end of the sheath, below the blue dots provided to guide the surgeon.

(13) Attach the mesh to the exterior apex of the vaginal wall with two or more sutures.

(14) Ensure the vaginal wall is in the appropriate anatomic position. If the cape is being used, lay the cape in the perirectal space, in a tension-free manner, and close the perirectal fascia over the mesh or the vaginal incision.

Figure 24:
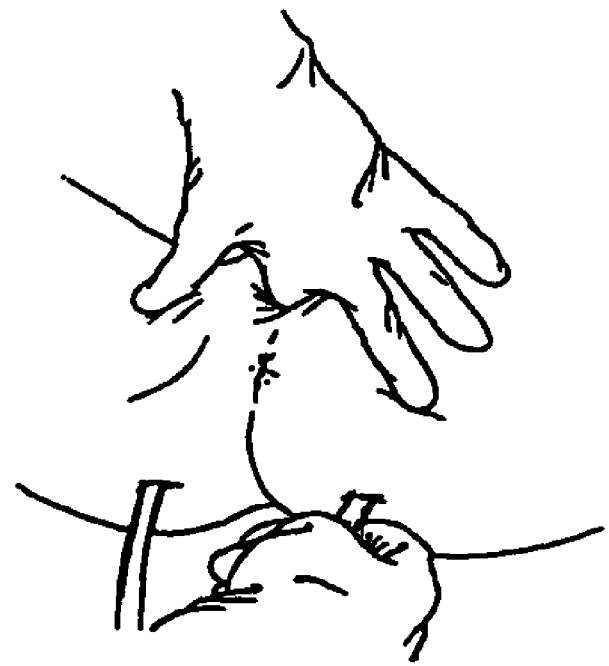
FIG. 24 illustrates positioning of the mesh by manipulating the sheathed end portions.

(15) Pull on the mesh assemblies to make final adjustments, as shown in FIG. 24.

(16) Remove plastic sheaths.

(17) Trim the mesh at the level of the subcutaneous tissue.

(18) Close the incisions.

(19) Use vaginal pack and antibiotic prophylaxis as appropriate.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

The invention claimed is:

1. A method for repair of vaginal vault prolapse in a patient, said method comprising the steps of:
    making a midline incision in an apex of a vagina;
    establishing a first pathway in tissue on a first side of said prolapsed organ, by:
        making a first incision lateral and posterior to the rectum in a skin of a buttocks, and
        passing a needle from said first incision toward said midline incision, by:
            palpating a tip of said needle distal and inferior to an ischial spine, and
            passing said needle through coccygeous muscle;
    establishing a second pathway in tissue on a contralateral side of said prolapsed organ, by:
        making a second incision lateral and posterior to the rectum in a skin of a buttocks on the contralateral side respective to said first incision, and
        passing a needle from said second incision toward said medial incision, by:
            palpating a tip of said needle distal and inferior to an ischial spine, and
            passing said needle through coccygeous muscle;
    positioning a support member in a position to reposition said vaginal vault in said vaginal vault's anatomically correct location, said supporting member comprising a support portion having a first and second end, and two end portions, said end portions respectively attached to said first end and said second end;

introducing said end portions through said first and second pathways, respectively; and adjusting said end portions so that said support member is in a therapeutic relationship to a tissue of said vaginal vault.

2. The method of claim 1, wherein introducing an end portion through a pathway comprises retracting back through the pathway a needle to which said end portion has been connected.

3. The method of claim 1, wherein adjusting said end portions so that said support member is in a therapeutic relationship to a tissue of said vaginal vault comprises:

attaching said support member to vaginal tissue with sutures;

ensuring the vaginal vault is in an appropriate anatomical position; and adjusting said support member by manipulation of said end portions.

4. The method of claim 1, wherein the implant includes exactly two elongated end portions.

5. A system for treating pelvic organ prolapse in a patient comprising an implant and a needle:

the implant comprising a support portion having first and second ends;

a first elongated end portion connected to said first end of said support portion;

a second elongated end portion connected to said second end of said support portion; and a connector at a distal end of at least one of the first elongated end portion and the second elongated end portion, and the needle having an end that connects to the connector wherein said support portion comprises a first and second long side and two short sides, wherein said first and second end portions are connected to said first and second long sides, respectively.

6. The system of claim 5, further comprising a repositioning means to effect tightening or loosening said first and second elongated end portions.

7. The system of claim 6, wherein said repositioning means comprises at least one filament threaded along at least one end portion.

8. The system of claim 6, wherein said repositioning means comprises at least one removable sheath on at least one end portion.

9. The system of claim 5, wherein said support portion is made from a polypropylene monofilament mesh.

10. The system of claim 5, wherein said support portion and said end portions are substantially comprised in a single article, wherein said support portion exhibits a width, the end portions exhibit a width, and the width of the support portion is greater than the width of the end portions.

11. The system of claim 5 wherein each of the first and second end portions comprises a connector configured to attach securely with the end of the needle.

12. The system of claim 11 wherein each of the first and second end portions comprises a removable sheath, and each connector is attached to a removable sheath.

13. The system of claim 5, wherein the implant includes exactly two elongated end portions.

14. A method for repair of pelvic organ prolapse in a patient, said method comprising the steps of:

providing an implant comprising a support portion having first and second ends, a first elongated end portion connected to said first end of said support portion, a second elongated end portion connected to second end of said support portion, and a connector at a distal end of at least one of the first elongated end portion and the second elongated end portion, positioning the support portion in a position to reposition said prolapsed organ in said organ's anatomically correct location;

providing a needle having an end that engages the connector, using the needle to establish a pathway in tissue on a first side of said prolapsed organ, said pathway extending from an external perirectal region to a region of an ischial spine of the patient;

following passage of the needle through the pathway, connecting the connector with the needle end; and retracting the needle through the pathway and external incision to place the at least one of said first elongated end portion and second elongated end portion at the pathway.

15. A method according to claim 14, wherein the implant comprises a connector at a distal end of at each of the first elongated end portion and the second elongated end portion, the method comprising:

using a needle to establish a first pathway in tissue on a first side of said prolapsed organ, said first pathway extending from a first external perirectal region to a region of an ischial spine of the patient;

following passage of the needle through the first pathway, connecting a first connector with the needle end;

retracting the needle through the first pathway and first external incision to place the end portion at the first pathway;

using a needle to establish a second pathway in tissue on a second side of said prolapsed organ, said second pathway extending from a second external perirectal region to a region of an ischial spine of the patient;

following passage of the needle through the second pathway, connecting a second connector with the needle end; and retracting the needle through the second pathway and second external incision to place the end portion at the second pathway.

16. The method of claim 14, wherein said support portion is wider relative to said end portions.

17. The method of claim 14, wherein each needle is arc-shaped.

18. The method of claim 14, wherein the implant includes exactly two elongated end portions.

19. A system for treating pelvic organ prolapse in a patient, the system comprising an implant and a needle:

the implant comprising a support portion having first and second ends;

a first elongated end portion connected to said first end of said support portion;

a second elongated end portion connected to said second end of said support portion; and a connector at a distal end of at least one of the first elongated end portion and the second elongated end portion, the needle having an end that connects to the connector, the system comprising a repositioning means to effect tightening or loosening said first and second elongated end portions, the repositioning means comprising at least one filament threaded along at least one end portion.

20. The system of claim 19, wherein said repositioning means comprises at least one removable sheath on at least one end portion, said support portion comprises a first and second long side and two short sides, wherein said first and second end portions are connected to said first and second long sides, respectively, and each of the first and second end portions comprises a connector configured to attach securely with the end of the needle.

21. An system for treating pelvic organ prolapse in a patient comprising an implant and a needle:

the implant comprising a support portion having first and second ends;

a first elongated end portion connected to said first end of said support portion;

a second elongated end portion connected to said second end of said support portion; and a connector at a distal end of at least one of the first elongated end portion and the second elongated end portion, and the needle having an end that connects to the connector, wherein the support portion and the end portions are substantially comprised in a single article, and the support portion exhibits a width, the end portions exhibits a width, and the width of the support portion is greater than the width of the end portions.

22. The system of claim 21, wherein the implant comprises repositioning means comprises at least one removable sheath on at least one end portion, and the support portion comprises a first and second long side and two short sides, and the first and second end portions are connected to the first and second long sides, respectively.

* * * * *